United States Patent
Xiao

(10) Patent No.: US 7,408,028 B2
(45) Date of Patent: Aug. 5, 2008

(54) PEPTIDES, ANTIBODIES THERETO, AND THEIR USE IN TREATMENT OF CENTRAL NERVOUS SYSTEM, DAMAGE

(75) Inventor: Zhi-Cheng Xiao, Singapore (SG)

(73) Assignee: Sinapore General Hospital Pte Ltd., Singapore (SG)

( * ) Notice: Subject to any disclaimer, the term of this patent is extended or adjusted under 35 U.S.C. 154(b) by 0 days.

(21) Appl. No.: 10/537,648

(22) PCT Filed: Dec. 5, 2003

(86) PCT No.: PCT/GB03/05323

§ 371 (c)(1),
(2), (4) Date: Jun. 6, 2005

(87) PCT Pub. No.: WO2004/052922

PCT Pub. Date: Jun. 24, 2004

(65) Prior Publication Data

US 2006/0205668 A1        Sep. 14, 2006

Related U.S. Application Data

(60) Provisional application No. 60/431,620, filed on Dec. 6, 2002.

(51) Int. Cl.
  *C07K 7/00*   (2006.01)
  *A61K 38/08*  (2006.01)
(52) U.S. Cl. .......................... 530/328; 530/329; 514/16
(58) Field of Classification Search ......... 530/328–329; 514/16
See application file for complete search history.

(56) References Cited

FOREIGN PATENT DOCUMENTS

WO    WO 97/02344       1/1997
WO    WO 01/51520 A2    7/2001

OTHER PUBLICATIONS

Sergel, T.A., et al. 2000 Journal of Virology 74(11): 5101-5107.*
Yuan, S-M., et al. 1998 Proteins: Structure, Function, and Genetics 30: 136-143.*
NINDS stroke reference sheets (3 pages).*
Sivakumaran, T.A. "Global Sequence Diversity of RB1 Gene"; EMBL Database Accession No. Q9BDQ2; XP-002279773 (2001).
Grandpre, T. "Nogo-66 receptor antagonist peptide promotes axonal regeneration"; Nature, 417: 547-551 (2002).
Fiedler, M. "An engineered IN-1 Fab fragment with improved affinity for the Nogo-A axonal growth inhibitor . . . "; Protein Engineering, 15(11): 931-941 (2002).
Karim, F. "Improving axonal growth and functional recovery after experimental spinal cord injury by neutralizing . . . "; Brain Research Reviews, 36: 204-212 (2001).
Huang, D.W. "A Therapeutic Vaccine Approach to Stimulate Axon Regeneration in the Adult Mammalian Spinal Cord"; Neuron, 24: 639-647 (1999).

* cited by examiner

*Primary Examiner*—Maryam Monshipouri
*Assistant Examiner*—Marsha M Tsay
(74) *Attorney, Agent, or Firm*—Dann, Dorfman, Herrell & Skillman; Kathleen D. Rigaut; Robert C. Netter

(57) ABSTRACT

The application provides peptides that interact with the inhibitory domains of the myelin proteins Nogo, TNR, and MAG. These may be used in the treatment of CNS damage, and for the development of further treatments. Also provided are methods and materials for immunizing subjects against the inhibitory domains of the myelin proteins, for the treatment of CNS damage.

5 Claims, 1 Drawing Sheet

Fig. 1

PCR primers

MAG1: 5- *CG* GGA TCC ATG ATA TTC CTT ACC ACC CT
            BamH I  Met

MAG2: 5- *TCC* C CGC GGC TCG GTG TGC TCC CTG AAA
              Sac II

TNR1: 5-*TCC* CC GCG GCA TGT CCA TGT GCC AGT TCA
             Sac II

TNR2: 5- *TT* GC GGC CGC TGG AGG GGC AAC TGC TGA
             Not I

NogoN1: 5-*TT* GCG GCC GCA ATG GAA GAC CTG GAC CAG TCT
              Not I

NogoN2: 5-*AAA* C TGC AGC CAC TGA GCC CGA GGA GCC CCT
               Pst I

Nogo66-1: 5-*AAA* CT GCA GCA AGG ATA TAC AAG GGT GT
                 Pst I

Nogo66-2: 5- *GC* TCT AGA TCA CTT CAG AGA ATC AAC TA
              Xba I  ***

Construct resulting from sequentially connected PCR products

Ala Ala Ala    Ala Ala Ala        Ala Ala Ala
5'-GGA TCC (MAG) GCC GCG GCA (TNR) GCG GCC GCA (NogoN) GCT GCA GCA
   BamH I          Sac II            Not I              Pst I

***
   (Nogo66) TGA TCT AGA-3'
                Xba I

SEQUENCE LISTING

```
<160> NUMBER OF SEQ ID NOS: 35

<210> SEQ ID NO 1
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 1

Tyr Leu Thr Gln Pro Gln Ser
1               5

<210> SEQ ID NO 2
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 2

Gly Ser Leu Pro His Ser Leu
1               5

<210> SEQ ID NO 3
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 3

Thr Gln Leu Phe Pro Pro Gln
1               5

<210> SEQ ID NO 4
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 4
```

```
His Ser Ile Pro Asp Asn Ile
  1               5

<210> SEQ ID NO 5
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 5

His His Met Pro His Asp Lys
  1               5

<210> SEQ ID NO 6
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 6

Tyr Thr Thr Pro Pro Ser Pro
  1               5

<210> SEQ ID NO 7
<211> LENGTH: 7
<212> TYPE: PRT
<213> ORGANISM: Artificial Sequence
<220> FEATURE:
<223> OTHER INFORMATION: From a phage library that displays random
      7-mers

<400> SEQUENCE: 7

Gln Leu Pro Leu Met Pro Arg
  1               5

<210> SEQ ID NO 8
<211> LENGTH: 508
<212> TYPE: PRT
<213> ORGANISM: Rattus norvegicus

<400> SEQUENCE: 8

Met Ile Phe Leu Thr Thr Leu Pro Leu Phe Trp Ile Met Ile Ser Ala
  1               5                  10                  15

Ser Arg Gly Gly His Trp Gly Ala Trp Met Pro Ser Ser Ile Ser Ala
             20                  25                  30

Phe Glu Gly Thr Cys Val Ser Ile Pro Cys Arg Phe Asp Phe Pro Asp
         35                  40                  45

Glu Leu Arg Pro Ala Val Val His Gly Val Trp Tyr Phe Asn Ser Pro
     50                  55                  60

Tyr Pro Lys Asn Tyr Pro Pro Val Val Phe Lys Ser Arg Thr Gln Val
 65                  70                  75                  80

Val His Glu Ser Phe Gln Gly Arg Ser Arg Leu Leu Gly Asp Leu Gly
                 85                  90                  95

Leu Arg Asn Cys Thr Leu Leu Leu Ser Thr Leu Ser Pro Glu Leu Gly
            100                 105                 110

Gly Lys Tyr Tyr Phe Arg Gly Asp Leu Gly Gly Tyr Asn Gln Tyr Thr
        115                 120                 125

Phe Ser Glu His Ser Val Leu Asp Ile Ile Asn Thr Pro Asn Ile Val
    130                 135                 140
```

```
Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
            165                 170                 175

His Glu Gly Leu Gly Glu Pro Thr Val Leu Gly Arg Leu Arg Glu Asp
        180                 185                 190

Glu Gly Thr Trp Val Gln Val Ser Leu Leu His Phe Val Pro Thr Arg
    195                 200                 205

Glu Ala Asn Gly His Arg Leu Gly Cys Gln Ala Ala Phe Pro Asn Thr
210                 215                 220

Thr Leu Gln Phe Glu Gly Tyr Ala Ser Leu Asp Val Lys Tyr Pro Pro
225                 230                 235                 240

Val Ile Val Glu Met Asn Ser Ser Val Glu Ala Ile Glu Gly Ser His
            245                 250                 255

Val Ser Leu Leu Cys Gly Ala Asp Ser Asn Pro Pro Pro Leu Leu Thr
        260                 265                 270

Trp Met Arg Asp Gly Met Val Leu Arg Glu Ala Val Ala Glu Ser Leu
    275                 280                 285

Tyr Leu Asp Leu Glu Glu Val Thr Pro Ala Glu Asp Gly Ile Tyr Ala
290                 295                 300

Cys Leu Ala Glu Asn Ala Tyr Gly Gln Asp Asn Arg Thr Val Glu Leu
305                 310                 315                 320

Ser Val Met Tyr Ala Pro Trp Lys Pro Thr Val Asn Gly Thr Val Val
            325                 330                 335

Ala Val Glu Gly Glu Thr Val Ser Ile Leu Cys Ser Thr Gln Ser Asn
        340                 345                 350

Pro Asp Pro Ile Leu Thr Ile Phe Lys Glu Lys Gln Ile Leu Ala Thr
    355                 360                 365

Val Ile Tyr Glu Ser Gln Leu Gln Leu Glu Leu Pro Ala Val Thr Pro
370                 375                 380

Glu Asp Asp Gly Glu Tyr Trp Cys Val Ala Glu Asn Gln Tyr Gly Gln
385                 390                 395                 400

Arg Ala Thr Ala Phe Asn Leu Ser Val Glu Phe Ala Pro Ile Ile Leu
            405                 410                 415

Leu Glu Ser His Cys Ala Ala Arg Asp Thr Val Gln Cys Leu Cys
        420                 425                 430

Val Val Lys Ser Asn Pro Glu Pro Ser Val Ala Phe Glu Leu Pro Ser
    435                 440                 445

Arg Asn Val Thr Val Asn Glu Thr Glu Arg Glu Phe Val Tyr Ser Glu
450                 455                 460

Arg Ser Gly Leu Leu Leu Thr Ser Ile Leu Thr Leu Arg Gly Gln Ala
465                 470                 475                 480

Gln Ala Pro Pro Arg Val Ile Cys Thr Ser Arg Asn Leu Tyr Gly Thr
            485                 490                 495

Gln Ser Leu Glu Leu Pro Phe Gln Gly Ala His Arg
        500                 505

<210> SEQ ID NO 9
<211> LENGTH: 205
<212> TYPE: PRT
<213> ORGANISM: Homo sapiens

<400> SEQUENCE: 9

Cys Pro Cys Ala Ser Ser Ala Gln Val Leu Gln Glu Leu Leu Ser Arg
```

-continued

```
              1               5                  10                 15
Ile Glu Met Leu Glu Arg Glu Val Ser Val Leu Arg Asp Gln Cys Asn
                20                 25                 30

Ala Asn Cys Cys Gln Glu Ser Ala Ala Thr Gly Gln Leu Asp Tyr Ile
                35                 40                 45

Pro His Cys Ser Gly His Gly Asn Phe Ser Phe Glu Ser Cys Gly Cys
 50                 55                 60

Ile Cys Asn Glu Gly Trp Phe Gly Lys Asn Cys Ser Glu Pro Tyr Cys
 65                 70                 75                 80

Pro Leu Gly Cys Ser Ser Arg Gly Val Cys Val Asp Gly Gln Cys Ile
                85                 90                 95

Cys Asp Ser Glu Tyr Ser Gly Asp Cys Ser Glu Leu Arg Cys Pro
                100                105                110

Thr Asp Cys Ser Ser Arg Gly Leu Cys Val Asp Gly Glu Cys Val Cys
                115                120                125

Glu Glu Pro Tyr Thr Gly Glu Asp Cys Arg Glu Leu Arg Cys Pro Gly
                130                135                140

Asp Cys Ser Gly Lys Gly Arg Cys Ala Asn Gly Thr Cys Leu Cys Glu
145                150                155                160

Glu Gly Tyr Val Gly Glu Asp Cys Gly Gln Arg Gln Cys Leu Asn Ala
                165                170                175

Cys Ser Gly Arg Gly Gln Cys Glu Glu Gly Leu Cys Val Cys Glu Glu
                180                185                190

Gly Tyr Gln Gly Pro Asp Cys Ser Ala Val Ala Pro Pro
                195                200                205

<210> SEQ ID NO 10
<211> LENGTH: 185
<212> TYPE: PRT
<213> ORGANISM: Homo sapiens

<400> SEQUENCE: 10

Met Glu Asp Leu Asp Gln Ser Pro Leu Val Ser Ser Ser Asp Ser Pro
 1               5                 10                 15

Pro Arg Pro Gln Pro Ala Phe Lys Tyr Gln Phe Val Arg Glu Pro Glu
                20                 25                 30

Asp Glu Glu Glu Glu Glu Glu Glu Glu Asp Glu Asp Glu Asp
                35                 40                 45

Leu Glu Glu Leu Glu Val Leu Glu Arg Lys Pro Ala Ala Gly Leu Ser
 50                 55                 60

Ala Ala Pro Val Pro Thr Ala Pro Ala Gly Ala Pro Leu Met Asp
 65                 70                 75                 80

Phe Gly Asn Asp Phe Val Pro Pro Ala Pro Arg Gly Pro Leu Pro Ala
                85                 90                 95

Ala Pro Pro Val Ala Pro Glu Arg Gln Pro Ser Trp Asp Pro Ser Pro
                100                105                110

Val Ser Ser Thr Val Pro Ala Pro Ser Pro Leu Ser Ala Ala Ala Val
                115                120                125

Ser Pro Ser Lys Leu Pro Glu Asp Asp Glu Pro Pro Ala Arg Pro Pro
                130                135                140

Pro Pro Pro Pro Ala Ser Val Ser Pro Gln Ala Glu Pro Val Trp Thr
145                150                155                160

Pro Pro Ala Pro Ala Pro Ala Ala Pro Pro Ser Thr Pro Ala Ala Pro
                165                170                175
```

```
Lys Arg Arg Gly Ser Ser Gly Ser Val
        180             185
```

<210> SEQ ID NO 11
<211> LENGTH: 66
<212> TYPE: PRT
<213> ORGANISM: Homo sapiens

<400> SEQUENCE: 11

```
Arg Ile Tyr Lys Gly Val Ile Gln Ala Ile Gln Lys Ser Asp Glu Gly
 1               5                  10                  15

His Pro Phe Arg Ala Tyr Leu Glu Ser Glu Val Ala Ile Ser Glu Glu
            20                  25                  30

Leu Val Gln Lys Tyr Ser Asn Ser Ala Leu Gly His Val Asn Cys Thr
        35                  40                  45

Ile Lys Glu Leu Arg Arg Leu Phe Leu Val Asp Asp Leu Val Asp Ser
    50                  55                  60

Leu Lys
65
```

<210> SEQ ID NO 12
<211> LENGTH: 973
<212> TYPE: PRT
<213> ORGANISM: Artificial Sequence
<220> FEATURE:
<223> OTHER INFORMATION: Fusion protein
<220> FEATURE:
<221> NAME/KEY: VARIANT
<222> LOCATION: (509)...(511)
<223> OTHER INFORMATION: Polyalanine linker
<220> FEATURE:
<221> NAME/KEY: VARIANT
<222> LOCATION: (717)...(719)
<223> OTHER INFORMATION: Polyalanine linker
<220> FEATURE:
<221> NAME/KEY: VARIANT
<222> LOCATION: (905)...(907)
<223> OTHER INFORMATION: Polyalanine linker

<400> SEQUENCE: 12

```
Met Ile Phe Leu Thr Thr Leu Pro Leu Phe Trp Ile Met Ile Ser Ala
 1               5                  10                  15

Ser Arg Gly Gly His Trp Gly Ala Trp Met Pro Ser Ser Ile Ser Ala
            20                  25                  30

Phe Glu Gly Thr Cys Val Ser Ile Pro Cys Arg Phe Asp Phe Pro Asp
            35                  40                  45

Glu Leu Arg Pro Ala Val Val His Gly Val Trp Tyr Phe Asn Ser Pro
    50                  55                  60

Tyr Pro Lys Asn Tyr Pro Pro Val Phe Lys Ser Arg Thr Gln Val
65                  70                  75                  80

Val His Glu Ser Phe Gln Gly Arg Ser Arg Leu Leu Gly Asp Leu Gly
            85                  90                  95

Leu Arg Asn Cys Thr Leu Leu Leu Ser Thr Leu Ser Pro Glu Leu Gly
            100                 105                 110

Gly Lys Tyr Tyr Phe Arg Gly Asp Leu Gly Gly Tyr Asn Gln Tyr Thr
            115                 120                 125

Phe Ser Glu His Ser Val Leu Asp Ile Ile Asn Thr Pro Asn Ile Val
        130                 135                 140

Val Pro Pro Glu Val Val Ala Gly Thr Glu Val Glu Val Ser Cys Met
145                 150                 155                 160

Val Pro Asp Asn Cys Pro Glu Leu Arg Pro Glu Leu Ser Trp Leu Gly
```

-continued

```
                    165                 170                 175
His Glu Gly Leu Gly Glu Pro Thr Val Leu Gly Arg Leu Arg Glu Asp
                180                 185                 190

Glu Gly Thr Trp Val Gln Val Ser Leu Leu His Phe Val Pro Thr Arg
            195                 200                 205

Glu Ala Asn Gly His Arg Leu Gly Cys Gln Ala Ala Phe Pro Asn Thr
        210                 215                 220

Thr Leu Gln Phe Glu Gly Tyr Ala Ser Leu Asp Val Lys Tyr Pro Pro
225                 230                 235                 240

Val Ile Val Glu Met Asn Ser Val Glu Ala Ile Glu Gly Ser His
                245                 250                 255

Val Ser Leu Leu Cys Gly Ala Asp Ser Asn Pro Pro Leu Leu Thr
            260                 265                 270

Trp Met Arg Asp Gly Met Val Leu Arg Glu Ala Val Ala Glu Ser Leu
            275                 280                 285

Tyr Leu Asp Leu Glu Glu Val Thr Pro Ala Glu Asp Gly Ile Tyr Ala
            290                 295                 300

Cys Leu Ala Glu Asn Ala Tyr Gly Gln Asp Asn Arg Thr Val Glu Leu
305                 310                 315                 320

Ser Val Met Tyr Ala Pro Trp Lys Pro Thr Val Asn Gly Thr Val Val
                325                 330                 335

Ala Val Glu Gly Glu Thr Val Ser Ile Leu Cys Ser Thr Gln Ser Asn
                340                 345                 350

Pro Asp Pro Ile Leu Thr Ile Phe Lys Glu Lys Gln Ile Leu Ala Thr
            355                 360                 365

Val Ile Tyr Glu Ser Gln Leu Gln Leu Glu Leu Pro Ala Val Thr Pro
        370                 375                 380

Glu Asp Asp Gly Glu Tyr Trp Cys Val Ala Glu Asn Gln Tyr Gly Gln
385                 390                 395                 400

Arg Ala Thr Ala Phe Asn Leu Ser Val Glu Phe Ala Pro Ile Ile Leu
                405                 410                 415

Leu Glu Ser His Cys Ala Ala Ala Arg Asp Thr Val Gln Cys Leu Cys
            420                 425                 430

Val Val Lys Ser Asn Pro Glu Pro Ser Val Ala Phe Glu Leu Pro Ser
        435                 440                 445

Arg Asn Val Thr Val Asn Glu Thr Glu Arg Glu Phe Val Tyr Ser Glu
        450                 455                 460

Arg Ser Gly Leu Leu Leu Thr Ser Ile Leu Thr Leu Arg Gly Gln Ala
465                 470                 475                 480

Gln Ala Pro Pro Arg Val Ile Cys Thr Ser Arg Asn Leu Tyr Gly Thr
                485                 490                 495

Gln Ser Leu Glu Leu Pro Phe Gln Gly Ala His Arg Ala Ala Ala Cys
            500                 505                 510

Pro Cys Ala Ser Ser Ala Gln Val Leu Gln Glu Leu Leu Ser Arg Ile
        515                 520                 525

Glu Met Leu Glu Arg Glu Val Ser Val Leu Arg Asp Gln Cys Asn Ala
        530                 535                 540

Asn Cys Cys Gln Glu Ser Ala Ala Thr Gly Gln Leu Asp Tyr Ile Pro
545                 550                 555                 560

His Cys Ser Gly His Gly Asn Phe Ser Phe Glu Ser Cys Gly Cys Ile
                565                 570                 575

Cys Asn Glu Gly Trp Phe Gly Lys Asn Cys Ser Glu Pro Tyr Cys Pro
            580                 585                 590
```

```
Leu Gly Cys Ser Ser Arg Gly Val Cys Val Asp Gly Gln Cys Ile Cys
            595                 600                 605

Asp Ser Glu Tyr Ser Gly Asp Cys Ser Glu Leu Arg Cys Pro Thr
    610                 615                 620

Asp Cys Ser Ser Arg Gly Leu Cys Val Asp Gly Glu Cys Val Cys Glu
625                 630                 635                 640

Glu Pro Tyr Thr Gly Glu Asp Cys Arg Glu Leu Arg Cys Pro Gly Asp
                645                 650                 655

Cys Ser Gly Lys Gly Arg Cys Ala Asn Gly Thr Cys Leu Cys Glu Glu
            660                 665                 670

Gly Tyr Val Gly Glu Asp Cys Gly Gln Arg Cys Leu Asn Ala Cys
        675                 680                 685

Ser Gly Arg Gly Gln Cys Glu Gly Leu Cys Val Cys Glu Glu Gly
    690                 695                 700

Tyr Gln Gly Pro Asp Cys Ser Ala Val Ala Pro Ala Ala Ala Met
705             710                 715                 720

Glu Asp Leu Asp Gln Ser Pro Leu Val Ser Ser Asp Ser Pro Pro
            725                 730                 735

Arg Pro Gln Pro Ala Phe Lys Tyr Gln Phe Val Arg Glu Pro Glu Asp
                740                 745                 750

Glu Glu Glu Glu Glu Glu Glu Glu Asp Glu Asp Glu Asp Leu
            755                 760                 765

Glu Glu Leu Glu Val Leu Glu Arg Lys Pro Ala Ala Gly Leu Ser Ala
770                 775                 780

Ala Pro Val Pro Thr Ala Pro Ala Ala Gly Ala Pro Leu Met Asp Phe
785                 790                 795                 800

Gly Asn Asp Phe Val Pro Pro Ala Pro Arg Gly Pro Leu Pro Ala Ala
                805                 810                 815

Pro Pro Val Ala Pro Glu Arg Gln Pro Ser Trp Asp Pro Ser Pro Val
        820                 825                 830

Ser Ser Thr Val Pro Ala Pro Ser Pro Leu Ser Ala Ala Val Ser
    835                 840                 845

Pro Ser Lys Leu Pro Glu Asp Asp Glu Pro Pro Ala Arg Pro Pro Pro
850                 855                 860

Pro Pro Pro Ala Ser Val Ser Pro Gln Ala Glu Pro Val Trp Thr Pro
865                 870                 875                 880

Pro Ala Pro Ala Pro Ala Ala Pro Pro Ser Thr Pro Ala Ala Pro Lys
                885                 890                 895

Arg Arg Gly Ser Ser Gly Ser Val Ala Ala Ala Arg Ile Tyr Lys Gly
            900                 905                 910

Val Ile Gln Ala Ile Gln Lys Ser Asp Glu Gly His Pro Phe Arg Ala
        915                 920                 925

Tyr Leu Glu Ser Glu Val Ala Ile Ser Glu Glu Leu Val Gln Lys Tyr
            930                 935                 940

Ser Asn Ser Ala Leu Gly His Val Asn Cys Thr Ile Lys Glu Leu Arg
945                 950                 955                 960

Arg Leu Phe Leu Val Asp Asp Leu Val Asp Ser Leu Lys
                965                 970
```

<210> SEQ ID NO 13
<211> LENGTH: 1524
<212> TYPE: DNA
<213> ORGANISM: Rattus norvegicus -continued

```
<400> SEQUENCE: 13
atgatattcc ttaccaccct gcctctgttt tggataatga tttcagcttc tcgagggggg      60
cactggggtg cctggatgcc ctcgtccatc tcagccttcg agggcacgtg tgtctccatc     120
ccctgccgtt tcgacttccc ggatgagctc agaccggctg tggtacatgg cgtctggtat     180
ttcaacagtc cctaccccaa gaactacccg ccagtggtct tcaagtcccg cacacaagtg     240
gtccacgaga gcttccaggg ccgtagccgc ctgttgggag acctgggcct acgaaactgc     300
accctgcttc tcagcacgct gagccctgag ctgggaggga aatactattt ccgaggtgac     360
ctgggcggct acaaccagta caccttctcg gagcacagcg tcctggacat catcaacacc     420
cccaacatcg tggtgccccc agaagtggtg gcaggaacgg aagtagaggt cagctgcatg     480
gtgccggaca actgcccaga gctgcgccct gagctgagct ggctgggcca cgaggggcta     540
ggggagccca ctgttctggg tcggctgcgg gaggatgaag gcacctgggt gcaggtgtca     600
ctgctacact tcgtgcctac tagagaggcc aacggccacc gtctgggctg tcaggctgcc     660
ttccccaaca ccaccttgca gttcgagggt tacgccagtc tggacgtcaa gtaccccccg     720
gtgattgtgg agatgaattc ctctgtggag gccattgagg gctcccacgt cagcctgctc     780
tgtggggctg acagcaaccc gccaccgctg ctgacttgga tgcgggatgg gatggtgttg     840
agggaggcag ttgctgagag cctgtacctg gatctggagg aggtgacccc agcagaggac     900
ggcatctatg cttgcctggc agagaatgcc tatggccagg acaaccgcac ggtggagctg     960
agcgtcatgt atgcaccttg gaagcccaca gtgaatggga cggtggtggc ggtagagggg    1020
gagacagtct ccatcctgtg ttccacacag agcaacccgg accctattct caccatcttc    1080
aaggagaagc agatcctggc cacggtcatc tatgagagtc agctgcagct ggaactccct    1140
gcagtgacgc ccgaggacga tggggagtac tggtgtgtag ctgagaacca gtatggccag    1200
agagccaccg ccttcaacct gtctgtggag tttgctccca taatccttct ggaatcgcac    1260
tgtgcagcgg ccagagacac cgtgcagtgc ctgtgtgtgg taaaatccaa cccggaaccc    1320
tccgtggcct ttgagctgcc ttcccgcaac gtgactgtga acgagacaga gagggagttt    1380
gtgtactcag agcgcagcgg cctcctgctc accagcatcc tcacgctccg gggtcaggcc    1440
caagccccac cccgcgtcat ttgtacctcc aggaacctct acggcaccca gagcctcgag    1500
ctgcctttcc agggagcaca ccga                                           1524

<210> SEQ ID NO 14
<211> LENGTH: 615
<212> TYPE: DNA
<213> ORGANISM: Homo sapiens

<400> SEQUENCE: 14
tgtccatgtg ccagttcagc ccaggtgctg caggagctgc tgagccggat cgagatgctg      60
gagagggagg tgtcggtgct gcgagaccag tgcaacgcca actgctgcca agaaagtgct     120
gccacaggac aactggacta tatccctcac tgcagtggcc acggcaactt tagctttgag     180
tcctgtggct gcatctgcaa cgaaggctgg tttggcaaga attgctcgga gccctactgc     240
ccgctgggtt gctccagccg gggggtgtgt gtggatggcc agtgcatctg tgacagcgaa     300
tacagcgggg atgactgttc cgaactccgg tgcccaacag actgcagctc ccgggggctc     360
tgcgtggacg gggagtgtgt ctgtgaagag ccctacactg gcgaggactg cagggaactg     420
aggtgccctg gggactgttc ggggaagggg agatgtgcca acgtacctg tttatgcgag     480 gagggctacg ttggtgagga ctgcggccag cggcagtgtc tgaatgcctg cagtgggcga    540
```

```
ggacaatgtg aggaggggct ctgcgtctgt gaagagggct accagggccc tgactgctca    600
gcagttgccc ctcca                                                     615

<210> SEQ ID NO 15
<211> LENGTH: 555
<212> TYPE: DNA
<213> ORGANISM: Homo sapiens

<400> SEQUENCE: 15
atggaagacc tggaccagtc tcctctggtc tcgtcctcgg acagcccacc ccggccgcag     60
cccgcgttca gtaccagtt cgtgagggag cccgaggacg aggaggaaga agaggaggag    120
gaagaggagg acgaggacga agacctggag gagctggagg tgctggagag gaagcccgcc    180
gccgggctgt ccgcggcccc agtgcccacc gccctgccg ccggcgcgcc cctgatggac    240
ttcggaaatg acttcgtgcc gccggcgccc cggggacccc tgccggccgc tcccccgtc     300 gccccggagc ggcagccgtc ttgggacccg agccggtgt cgtcgaccgt gcccgcgcca    360
tccccgctgt ctgctgccgc agtctcgccc tccaagctcc ctgaggacga cgagcctccg    420
gcccggcctc ccctcctcc ccggccagc gtgagccccc aggcagagcc cgtgtggacc     480
ccgccagccc cggctcccgc cgcgccccc tccaccccgg ccgcgcccaa gcgcaggggc     540
tcctcgggct cagtg                                                    555

<210> SEQ ID NO 16
<211> LENGTH: 198
<212> TYPE: DNA
<213> ORGANISM: Homo sapiens

<400> SEQUENCE: 16
aggatataca agggtgtgat ccaagctatc cagaaatcag atgaaggcca cccattcagg     60
gcatatctgg aatctgaagt tgctatatct gaggagttgg ttcagaagta cagtaattct    120
gctcttggtc atgtgaactg cacgataaag gaactcaggc gcctcttctt agttgatgat    180
ttagttgatt ctctgaag                                                 198

<210> SEQ ID NO 17
<211> LENGTH: 28
<212> TYPE: DNA
<213> ORGANISM: Artificial Sequence
<220> FEATURE:
<223> OTHER INFORMATION: PCR primer MAG1

<400> SEQUENCE: 17
cgggatccat gatattcctt accaccct                                       28

<210> SEQ ID NO 18
<211> LENGTH: 28
<212> TYPE: DNA
<213> ORGANISM: Artificial Sequence
<220> FEATURE:
<223> OTHER INFORMATION: PCR primer MAG2

<400> SEQUENCE: 18
tccccgcggc tcggtgtgct ccctggaa                                       28

<210> SEQ ID NO 19
<211> LENGTH: 29
<212> TYPE: DNA
<213> ORGANISM: Artificial Sequence
<220> FEATURE:
```

```
<223> OTHER INFORMATION: PCR primer TNR1

<400> SEQUENCE: 19
tccccgcggc atgtccatgt gccagttca                                           29

<210> SEQ ID NO 20
<211> LENGTH: 28
<212> TYPE: DNA
<213> ORGANISM: Artificial Sequence
<220> FEATURE:
<223> OTHER INFORMATION: PCR primer TNR2

<400> SEQUENCE: 20
ttgcggccgc tggaggggca actgctga                                            28

<210> SEQ ID NO 21
<211> LENGTH: 32
<212> TYPE: DNA
<213> ORGANISM: Artificial Sequence
<220> FEATURE:
<223> OTHER INFORMATION: PCR primer NogoN1

<400> SEQUENCE: 21
ttgcggccgc aatggaagac ctggaccagt ct                                       32

<210> SEQ ID NO 22
<211> LENGTH: 31
<212> TYPE: DNA
<213> ORGANISM: Artificial Sequence
<220> FEATURE:
<223> OTHER INFORMATION: PCR primer NogoN2

<400> SEQUENCE: 22
aaactgcagc cactgagccc gaggagcccc t                                        31

<210> SEQ ID NO 23
<211> LENGTH: 28
<212> TYPE: DNA
<213> ORGANISM: Artificial Sequence
<220> FEATURE:
<223> OTHER INFORMATION: PCR primer Nogo66-1

<400> SEQUENCE: 23
aaactgcagc aaggatatac aagggtgt                                            28

<210> SEQ ID NO 24
<211> LENGTH: 28
<212> TYPE: DNA
<213> ORGANISM: Artificial Sequence
<220> FEATURE:
<223> OTHER INFORMATION: PCR primer Nogo66-2

<400> SEQUENCE: 24
gctctagatc acttcagaga atcaacta                                            28

<210> SEQ ID NO 25
<211> LENGTH: 2934
<212> TYPE: DNA
<213> ORGANISM: Artificial Sequence
<220> FEATURE:
<223> OTHER INFORMATION: Construct resulting from sequentially connected
      PCR products

<400> SEQUENCE: 25
ggatccatga tattccttac caccctgcct ctgttttgga taatgatttc agcttctcga         60
```

```
ggggggcact ggggtgcctg gatgccctcg tccatctcag ccttcgaggg cacgtgtgtc      120
tccatcccct gccgtttcga cttcccggat gagctcagac cggctgtggt acatggcgtc      180
tggtatttca acagtcccta ccccaagaac tacccgccag tggtcttcaa gtcccgcaca      240
caagtggtcc acgagagctt ccagggccgt agccgcctgt tgggagacct gggcctacga      300
aactgcaccc tgcttctcag cacgctgagc cctgagctgg gagggaaata ctatttccga      360
ggtgacctgg gcggctacaa ccagtacacc ttctcggagc acagcgtcct ggacatcatc      420
aacaccccca acatcgtggt gcccccagaa gtggtggcag gaacggaagt agaggtcagc      480
tgcatggtgc cggacaactg cccagagctg cgccctgagc tgagctggct gggccacgag      540
gggctagggg agcccactgt tctgggtcgg ctgcgggagg atgaaggcac ctgggtgcag      600
gtgtcactgc tacacttcgt gcctactaga gaggccaacg ccaccgtct gggctgtcag       660 gctgccttcc ccaacaccac cttgcagttc gagggttacg ccagtctgga cgtcaagtac      720
cccccggtga ttgtggagat gaattcctct gtggaggcca ttgagggctc ccacgtcagc      780
ctgctctgtg gggctgacag caacccgcca ccgctgctga cttggatgcg ggatgggatg      840
gtgttgaggg aggcagttgc tgagagcctg tacctggatc tggaggaggt gaccccagca      900
gaggacggca tctatgcttg cctggcagag aatgcctatg ccaggacaa ccgcacggtg       960 gagctgagcg tcatgtatgc accttggaag cccacagtga atgggacggt ggtggcggta     1020
gaggggagag cagtctccat cctgtgttcc acacagagca acccggaccc tattctcacc     1080
atcttcaagg agaagcagat cctggccacg gtcatctatg agagtcagct gcagctggaa     1140
ctccctgcag tgacgcccga ggacgatggg gagtactggt gtgtagctga gaccagtat      1200 ggccagagag ccaccgcctt caacctgtct gtggagtttg ctcccataat ccttctggaa     1260
tcgcactgtg cagcggccag agacaccgtg cagtgcctgt gtgtggtaaa atccaacccg     1320
gaaccctccg tggcctttga gctgccttcc cgcaacgtga ctgtgaacga cagagagg       1380 gagtttgtgt actcagagcg cagcggcctc ctgctcacca gcatcctcac gctccggggt     1440
caggcccaag cccccaccccg cgtcatttgt acctccagga acctctacgg cacccagagc    1500
ctcgagctgc ctttccaggg agcacaccga gccgcggcat gtccatgtgc cagttcagcc     1560
caggtgctgc aggagctgct gagccggatc gagatgctgg agaggaggt gtcggtgctg      1620 cgagaccagt gcaacgccaa ctgctgccaa gaaagtgctg ccacaggaca actggactat    1680
atccctcact gcagtggcca cggcaacttt agctttgagt cctgtggctg catctgcaac    1740
gaaggctggt ttggcaagaa ttgctcggag ccctactgcc cgctgggttg ctccagccgg    1800
ggggtgtgtg tggatggcca gtgcatctgt gacagcgaat acagcgggga tgactgttcc    1860
gaactccggt gcccaacaga ctgcagctcc cgggggctct gctggacgg ggagtgtgtc     1920 tgtgaagagc cctacactgg cgaggactgc agggaactga ggtgccctgg ggactgttcg    1980
gggaagggga gatgtgccaa cggtacctgt ttatgcgagg agggctacgt tggtgaggac    2040
tgcggccagc ggcagtgtct gaatgcctgc agtgggcgag acaatgtga ggagggctc      2100 tgcgtctgtg aagagggcta ccagggccct gactgctcag cagttgcccc tccagcggcc    2160
gcaatggaag acctggacca gtctcctctg gtctcgtcct cggacagccc accccggccg    2220
cagcccgcgt tcaagtacca gttcgtgagg agcccgagg acgaggagga agaagaggag     2280
gaggaagagg aggacgagga cgaagacctg gaggagctgg aggtgctgga ggaagcccc     2340 gccgccgggc tgtccgcggc cccagtgccc accgccctg ccgccggcgc gccctgatg       2400 gacttcggaa atgacttcgt gccgccggcg ccccggggac ccctgccggc cgctcccccc     2460
```

```
gtcgccccgg agcggcagcc gtcttgggac ccgagcccgg tgtcgtcgac cgtgcccgcg    2520
ccatccccgc tgtctgctgc cgcagtctcg ccctccaagc tccctgagga cgacgagcct    2580
ccggcccggc ctccccctcc tccccggcc agcgtgagcc cccaggcaga gcccgtgtgg     2640
accccgccag ccccggctcc cgccgcgccc cctccaccc cggccgcgcc caagcgcagg     2700
ggctcctcgg gctcagtggc tgcagcaagg atatacaagg gtgtgatcca agctatccag    2760
aaatcagatg aaggccaccc attcagggca tatctggaat ctgaagttgc tatatctgag    2820
gagttggttc agaagtacag taattctgct cttggtcatg tgaactgcac gataaaggaa    2880
ctcaggcgcc tcttcttagt tgatgattta gttgattctc tgaagtgatc taga          2934

<210> SEQ ID NO 26
<211> LENGTH: 42
<212> TYPE: DNA
<213> ORGANISM: M13 coliphage

<400> SEQUENCE: 26
ttattcgcaa ttcctttagt ggtacctttc tattctcact ct                        42

<210> SEQ ID NO 27
<211> LENGTH: 33
<212> TYPE: DNA
<213> ORGANISM: M13 coliphage

<400> SEQUENCE: 27
ggtggaggtt cggccgaaac tgttgaaagt tgt                                  33

<210> SEQ ID NO 28
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 28
tatctgacgc agcctcagtc g                                               21

<210> SEQ ID NO 29
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 29
ggttctctgc ctcattcgct g                                               21

<210> SEQ ID NO 30
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 30
acgcagctgt ttcctcctta g                                               21

<210> SEQ ID NO 31
<211> LENGTH: 21
<212> TYPE: DNA
<213> ORGANISM: Artificial Sequence
<220> FEATURE:
```

```
<223> OTHER INFORMATION: Exemplary 7-mer peptide-encoding sequence

<400> SEQUENCE: 31
cattctattc ctgataatat t                                              21

<210> SEQ ID NO 32
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 32
catcatatgc ctcatgataa g                                              21

<210> SEQ ID NO 33
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 33
tatacgacgc ctccgagtcc t                                              21

<210> SEQ ID NO 34
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 34
cagcttccgc ttatgcctcg t                                              21

<210> SEQ ID NO 35
<211> LENGTH: 21
<212> TYPE: DNA
<213> ORGANISM: Artificial Sequence
<220> FEATURE:
<223> OTHER INFORMATION: Exemplary 7-mer peptide-encoding sequence

<400> SEQUENCE: 35
acgcagctgt ttcctcctca g                                              21
```

PEPTIDES, ANTIBODIES THERETO, AND THEIR USE IN TREATMENT OF CENTRAL NERVOUS SYSTEM, DAMAGE

This application is a §371 application of PCT/GB2003/005323 filed 5 Dec. 2003, which in turn claims priority to U.S. Provisional Application 60/431,620 filed 6 Dec. 2002, now abandoned. Each of the above identified applications is incorporated by reference herein.

The invention relates to materials and methods useful in the treatment of, or in the development of treatments for, CNS damage, e.g. spinal cord injury or stroke.

BACKGROUND

Most tissues in the body, such as skin, liver and peripheral nerve, have a remarkable ability to repair themselves after injury. By contrast, the central nervous system (CNS)—including the brain and the spinal cord—has little innate capacity for repair. When axonal connections are damaged in the adult brain or spinal cord, they show an extremely limited ability to regenerate, even though axons can grow and regenerate efficiently in the embryonic CNS and in the adult peripheral nervous system. Factors that account for the inability of CNS axons to regenerate can be grouped in two categories: intrinsic properties of CNS neurons that may make them incapable of regeneration; and extrinsic factors in the CNS environment that are inhibitory to axonal elongation.

The idea that factors in the CNS environment can prevent regeneration dates back to the early $20^{th}$ century. Ramon y Cajal observed that the inability of adult CNS neurons to extend axonal processes could be overcome by giving them the permissive environment of a peripheral nerve. Then, about 20 years ago, David and Aguayo showed that retinal neurons could form long projections in peripheral nerve grafts. Later, Schwab discovered that dorsal root ganglion neurons in culture extend their axons across Schwann cells but avoid oligodendrocytes and the fatty myelin sheath (Schwab et al 1993).

These results show that failure to regenerate is not purely an intrinsic deficit of CNS neurons, and inhibitory factors in the CNS environment also play an important role. These inhibitory factors are mainly located in the glial scar that forms at the region of injury and by the myelin that ensheaths axons in the white matter tracks.

Following CNS injury, the central area of necrosis is infiltrated by glia and other non-neuronal cells, and a fibrous scar forms. Axons do not extend through the scar and their growth appears to be inhibited by it. Molecular components that may contribute to this inhibitory activity include the extracellular matrix glycoprotein tenascin-R (TN-R) and the myelin-associated neurite outgrowth inhibitors myelin-associated glycoprotein (MAG) and Nogo.

TN-R

TN-R has been implicated in a variety of cell-matrix interactions involved in the molecular control of axon guidance and neural cell migration during development and regeneration of CNS (reviewed by Erickson, 1993; Chiquet-Ehrismann et al., 1994; Pesheva et al., 2000; 2001). TN-R is the smallest member of the tenascin family and is composed of four structural motifs: a cysteine-rich segment at the N-terminus is followed by 4.5 EGF-like repeats. This region is followed by 9 consecutive fibronectin type III-like domains and at the C-terminus TN-R is related to the beta- and gamma-chains of fibrinogen.

TN-R is expressed predominantly by oligodendrocytes during the onset and early phases of myelin formation, and remains expressed by some oligodendrocytes in the adult. TN-R is also expressed in some neurons and interneurons in the spinal cord, retina, cerebellum, and hippocampus (Fuss et al., 1991; 1993). TN-R co-localizes with other glial-derived molecules (i.e. myelin-associated glycoprotein and a phosphacan-related molecule) at high density in the nodes of Ranvier of CNS myelinated axons (Xiao et al., 1997; Yang et al, 1999).

TN-R can inhibit or promote neurite outgrowth, depending on the neuronal cell type and the environment in which it is presented. When TN-R was offered, acting as a sharp substrate boundary, dorsal root ganglion (DRG), cerebellum and retinal ganglion neuron growth cones avoided growing on these molecules, but were not induced to collapse. On the other hand, when TN-R was offered in a mixture with laminin (which strongly promotes growth of embryonic and adult axons) as a uniform substrate, DRG growth cones displayed a collapsed morphology and were able to advance at a faster rate than on laminin alone.

Using several monoclonal antibodies binding to distinct epitopes on the tenascin molecule, epidermal growth factor-like (EGF-L) repeats and fibronectin type III homologous repeats 4-5 were identified to be responsible for growth cone repulsion.

In vitro, outgrowth of embryonic and adult retinal ganglion cell axons from mouse retinal explants is significantly reduced on homogeneous substrates of tenascin-R or a bacterially expressed tenascin-R fragment comprising the EGF-L domain. When both molecules are presented, acting as a sharp substrate boundary, regrowing adult axons do not cross into the territory containing tenascin-R or EGF-L. All in vitro experiments were done in the presence of laminin, suggesting that tenascin-R and EGF-L actively inhibit axonal growth. Neurites and growth cones were repelled from areas coated with fragments containing the EGF-L (the amino-terminal cysteine-rich domain plus the EGF-like repeats), FN (fibronectin) 1-2, FN3-5 and FG (fibrinogen) domains of TN-R, and EGF-L prevents neurite outgrowth of hippocampal neurons.

TN-R also induces axonal defasciculation in vitro through the EGF-L domain (Taylor et al., 1993; Xiao et al., 1996, 1997, 1998; Becker et al, 1999; Becker et al, 2000).

After 3-acetylpyridine-induced lesion of the olivocerebellar system of the adult rat, the density of cells containing TN-R transcripts increased significantly in the inferior olivary nucleus and in the white matter of the cerebellar cortex. Immunohistochemical investigations confirmed these observations at the protein level.

After a spinal cord mechanical lesion of rat, TN-R mRNA was also upregulated (Wintergerst at al, 1997; Deckner et al, 2000).

These findings suggested that the continued overexpression of TN-R in the injured CNS may contribute to the failure of adult axonal regeneration in vivo.

Tenascin-R is a member of the tenascin family, which play important roles in cell interactions in the developing nervous system, such as neuronal migration, neuritogenesis, and neuronal regeneration. Tenascin-R is expressed predominantly by oligodendrocytes during the onset and early phases of myelin formation, and remain expressed by some oligodendrocytes in the adult (Pesheva et. al., 1989; Fuss et al., 1991, 1993; Wintergerst et. al., 1993; Ajemian A. et. al., 1994). TN-R is a multi-functional molecule (Lochter and Schachner, 1993; Pesheva et. al., 1993; Taylor et. al., 1993; Xiao et. al., 1996, 1997,1998), and it has indicated that it is an inhibitory component of myelin extraction. Xiao have found that, the EGF-L domain of TN-R can inhibit the neurite outgrowth.

MAG

MAG is a transmembrane protein of the immunoglobulin superfamily expressed by myelinating glial cells of the central and peripheral nervous systems, where MAG represents 1 and 0.1% of the total myelin proteins, respectively (Heape at al, 1999). MAG is a potent inhibitor of axonal regeneration and also, depending on the age and type of neuron, can promote axonal growth. MAG inhibits neurite outgrowth of retinal, superior cervical ganglion, spinal, and hippocampal and dorsal root ganglion (DRG) neurons of all postnatal ages, but can enhance neurite outgrowth of embryonic spinal cord neurons and newborn DRG neurons (DeBellard at al, 1996; Turnley et al, 1998; Shen et al, 1998; Yang et al, 1999).

MAG can also induce growth cone collapse. 60% of axonal growth cones of postnatal day 1 hippocampal neurons collapsed when they encountered coated recombinant MAG (rMAG). Such collapse was not observed with denatured rMAG (Li et al, 1996). Soluble dMAG (a proteolytic fragment of the extracellular domain of MAG, which is released in abundance from myelin and found in vivo) and chimeric MAG-Fc can potently inhibit neurite outgrowth from P6 DRG neurons. This inhibition was blocked when a MAG monoclonal antibody was included.

These results indicate that soluble dMAG detected in vivo could contribute to the lack of regeneration in the mammalian CNS after injury (Tang et al, 1997; 2001).

MAG has two recognition sites for neurons, the sialic acid binding site at R118 and a distinct inhibition site which is absent from the first three Ig domains (Tang et al, 1997).

MAG is a well characterized member of the immunoglobulin gene superfamily, and it exerts a robust inhibitory effect on neurite outgrowth from young cerebellar neurons and adult dorsal ganglion (DRG) neurons (Mukhopadhyay et al., 1994). MAG is a membrane protein with 626 amino acids. It has been reported that soluble MAG, which consists of the extracellular domain, has an inhibitory effect on neurite outgrowth (Mckerracher et. al., 1994). The extracellular domain of MAG consists of five Ig-like domains, and it is demonstrated that the first two Ig-like domains are important for the interaction between MAG and neuronal membrane, while the other three Ig-like domains might be involved in the inhibitory effects (Collins et al., 1997).

Nogo

Nogo is a high molecular weight integral membrane protein that localizes to CNS myelin, but not PNS myelin. Nogo has three isoforms, named Nogo-A, -B and -C, which are generated by alternative splicing. NI-250 and NI-35 were first identified and named as the 2 isoforms of Nogo; it has now been established that NI-250 is Nogo-A and NI-35 is Nogo-B. Nogo is expressed by oligodendrocytes in white matter of the CNS and is found in the inner and outer leaflets of myelin and in the endoplasmic reticulum.

In vitro characterization of Nogo has demonstrated its function as a potent inhibitor of axon elongation. In vivo neutralization of Nogo activity results in enhanced axonal regeneration and functional recovery following CNS injury as well as increased plasticity in uninjured CNS fibers. The monoclonal antibody mAb IN-1 was shown to promote long-distance regeneration and functional recovery in vivo when applied to spinal cord-injured adult rat (Chen et al, 2000; GrandPre et al; Merkler et al).

These findings suggest that Nogo may be a major contributor to the nonpermissive nature of the CNS environment. Two distinct inhibitory domains of Nogo have been identified: an intracellular amino-terminal domain (NogoN) of Nogo A and a short 66 residue region (Nogo-66) located between two hydrophobic domains of the three isoforms, Nogo-A, Nogo-B and Nogo-C (Chen et al, 2000; GrandPre et al, 2000; Fournier et al , 2001; Filbin, 2003). These domains are illustrated in Science, Vol 297 (5584), 16 Aug. 2002, p. 1132-1134.

Nogo-A is expressed by oligodendrocytes but not by Schwann cells. It can inhibit axonal extension and collapses dorsal root ganglion growth cones (GrandPre et. al., 2000). The neurite outgrowth inhibitory activity of Nogo can be neutralized by monoclonal antibody IN-1, which allows axonal regeneration and functional recovery after spinal cord injury (Chen et. al., 2000). Nogo is a membrane protein with 1163 amino acids. The C-terminal tail contains two hydrophobic transmembrane domains separated by a 66-residue hydrophilic extracellular domain. This 66-residue extracellular domain can inhibit axon outgrowth (Fournier et. al., 2001).

Huang et al. (1999) discloses a therapeutic vaccine approach to stimulate axonal regeneration in the adult spinal cord.

It is an object of the invention to provide materials and methods useful in the treatment of, or in the development of treatments for, CNS damage, e.g. spinal cord injury, by overcoming the inhibitory effects of myelin on axonal regeneration.

SUMMARY OF THE INVENTION

In a first general aspect, the inventor proposes using molecules which interact with the inhibitory domains of major myelin proteins as an adjunct treatment for CNS damage, and for the development of further treatments.

In a second general aspect, the inventor proposes immunizing subjects with the inhibitory domains of major myelin proteins as an adjunct treatment for CNS damage.

It may appear impractical to immunize subjects against myelin antigens, as this approach may induce autoimmune demyelinating disease, leading to unacceptable side effects. Also, some myelin antibodies promote remyelination (Rodriguez et al., 1987), which is not of benefit during axonal regeneration. The inventor's approach is, however, to base the vaccine on the specific inhibitory portions of major myelin proteins, instead of whole myelin proteins. Antibodies raised against the inhibitory portions will block the inhibitory effect of myelin on axonal regeneration.

First Aspect

Accordingly, the invention provides a peptide, the amino acid sequence of which consists of an amino acid sequence selected from the group consisting of:

YLTQPQS;        (SEQ ID NO. 1)

GSLPHSL;        (SEQ ID NO. 2)

TQLFPPQ;        (SEQ ID NO. 3)

HSIPDNI;        (SEQ ID NO. 4)

HHMPHDK;        (SEQ ID NO. 5)

YTTPPSP;        (SEQ ID NO. 6)
and

QLPLMPR.        (SEQ ID NO. 7)

These sequences each represent the deduced amino acid sequences of several peptides that have been identified by phage display as being capable of binding to one or more of the neuronal growth inhibitory molecules Nogo (specifically, the Nogo-66 domain), MAG and TN-R (specifically, TNR-EGFL).

SEQ ID NO. 1 represents the sequence of 43 identical peptides capable of binding to Nogo-66, and also the sequence of 19 identical peptides capable of binding to MAG.

SEQ ID NO. 2 represents the sequence of 8 identical peptides capable of binding to Nogo-66.

SEQ ID NO. 3 represents the sequence of 18 identical peptides capable of binding to TNR-EGFL.

SEQ ID NO. 4 represents the sequence of 3 identical peptides capable of binding to TNR-EGFL.

SEQ ID NO. 5 represents the sequence of 1 peptide capable of binding to TNR-EGFL.

SEQ ID NO. 6 represents the sequence of 1 peptide capable of binding to TNR-EGFL.

SEQ ID NO. 7 represents the sequence of 5 identical peptides capable of binding to MAG.

Of these, SEQ ID NO. 1 has been shown by phage binding to block the inhibitory effects of Nogo-66 and MAG on neuronal cell adhesion in an in vitro assay. Similarly, SEQ ID NO. 3 has been shown to block the inhibitory effect of TNR-EGFL. A preferred peptide therefore consists of SEQ ID NO. 1; another preferred peptide consists of SEQ ID NO. 3.

The invention further provides a peptide up to 60 amino acids in length comprising an amino acid sequence selected from the group consisting of:

| | |
|---|---|
| YLTQPQS; | (SEQ ID NO. 1) |
| GSLPHSL; | (SEQ ID NO. 2) |
| TQLFPPQ; | (SEQ ID NO. 3) |
| HSIPDNI; | (SEQ ID NO. 4) |
| HHMPHDK; | (SEQ ID NO. 5) |
| YTTPPSP; and | (SEQ ID NO. 6) |
| QLPLMPR, | (SEQ ID NO. 7) | wherein the peptide is capable of binding to Nogo (preferably Nogo-66), MAG and/or TN-R (preferably TNR-EGFL).

Preferably, the peptide is up to 50 amino acids in length, more preferably up to 40, up to 30, up to 25, up to 20, up to 19, up to 18, up to 17, up to 16, up to 15, up to 14, up to 13, up to 12, up to 11, up to 10, up to 9, or up to 8 amino acids in length.

A preferred peptide comprises SEQ ID NO. 1; another preferred peptide comprises SEQ ID NO. 3.

The invention further provides a peptide up to 60 amino acids in length comprising an amino acid sequence having at least 5 residues identical with corresponding residues in an amino acid sequence selected from the group consisting of:

| | |
|---|---|
| YLTQPQS; | (SEQ ID NO. 1) |
| GSLPHSL; | (SEQ ID NO. 2) |
| TQLFPPQ; | (SEQ ID NO. 3) |
| HSIPDNI; | (SEQ ID NO. 4) |
| HHMPHDK; | (SEQ ID NO. 5) |
| YTTPPSP; and | (SEQ ID NO. 6) |
| QLPLMPR, | (SEQ ID NO. 7) | wherein the peptide is capable of binding to Nogo (preferably Nogo-66), MAG and/or TN-R (preferably TNR-EGFL).

Preferred sizes of the peptide are as stated previously. Peptides having at least 5 residues identical with corresponding residues of SEQ ID NO. 1, or at least 5 residues identical with corresponding residues of SEQ ID NO. 3 are preferred.

Preferably the minimum number of identical residues is 6.

The invention further provides a composition comprising one or more peptides of the invention, together with one or more pharmaceutically acceptable ingredients.

Preferably the composition is formulated for injection in vivo, preferably for direct injection into the CNS.

The invention further provides a peptide of the invention for use in a method of treatment. Such use may be in the treatment of CNS damage, especially spinal cord injury and stroke.

The invention also provides the use of a peptide of the invention in the preparation of a medicament for the treatment of CNS damage, especially spinal cord injury and stroke.

The invention also provides a method for treating CNS damage, the method comprising administering a peptide of the invention to a patient at or near a site of CNS damage in the patient. Specifically, the invention provides a method for treating SCI or stroke, the method comprising administering to a patient a peptide having an amino acid sequence that consists of SEQ ID NO. 1 or 3, by direct injection into a site of SCI or stroke damage in the patient.

The invention also provides the use of a peptide of the invention and/or a computer-generated model thereof, in the design of a mimetic capable of binding to one or more of the neuronal growth inhibitory molecules Nogo (preferably Nogo-66), MAG and/or TN-R (preferably TNR-EGFL).

Similarly, the invention provides a method of designing a mimetic of a peptide of the invention, the mimetic being capable of binding to one or more of the neuronal growth inhibitory molecules Nogo (preferably Nogo-66), MAG and/or TN-R (preferably TNR-EGFL), said method comprising:

(i) analysing a peptide of the invention that is capable of binding to one or more of the neuronal growth inhibitory molecules Nogo (preferably Nogo-66), MAG and/or TN-R (preferably TNR-EGFL) to determine the amino acid residues essential and important for the activity to define a pharmacophore; and (ii) modelling the pharmacophore to design and/or screen candidate mimetics having the biological activity.

Preferably the method and/or use includes a step of assaying binding of a candidate mimetic to Nogo (preferably Nogo-66), MAG and/or TN-R (preferably TNR-EGFL) in vitro. Having identified a candidate mimetic that is capable of such in vitro binding, the candidate mimetic is preferably optimised for in vivo use. Following such optimisation, the optimised mimetic is preferably formulated together with one or more pharmaceutically acceptable ingredients.

The invention further provides a bacteriophage which expresses a fusion protein consisting of a peptide and a bacteriophage coat protein, such that the peptide is displayed on the surface of the bacteriophage virion, wherein the peptide is up to 60 amino acids in length and comprises an amino acid sequence having at least four residues identical with corresponding residues of an amino acid sequence selected from the group consisting of:

| | |
|---|---|
| YLTQPQS; | (SEQ ID NO. 1) |
| GSLPHSL; | (SEQ ID NO. 2) |
| TQLFPPQ; | (SEQ ID NO. 3) |
| HSIPDNI; | (SEQ ID NO. 4) |
| HHMPHDK; | (SEQ ID NO. 5) |
| YTTPPSP; and | (SEQ ID NO. 6) |
| QLPLMPR. | (SEQ ID NO. 7) |

Preferably the peptide of the invention is up to 50 amino acids in length, more preferably up to 40, up to 30, up to 25, up to 20, or up to 15 amino acids in length. Still more preferably, the peptide of the invention is 8-12 amino acids in length, more preferably 6-10. Preferably the minimum number of identical residues is 5 or 6.

The invention further provides a screening method for peptides capable of binding to Nogo (preferably Nogo-66), MAG and/or TN-R (preferably TNR-EGFL), the method comprising:
providing bacteriophages of the invention, respectively expressing different peptides; and
screening the bacteriophages for the ability to bind to Nogo (preferably Nogo-66), MAG and/or TN-R (preferably TNR-EGFL).

Bacteriophages which are identified as being capable of binding to Nogo (preferably Nogo-66), MAG and/or TN-R (preferably TNR-EGFL), or the peptides they display, may then be screened for the ability to block the inhibitory effects of Nogo (preferably Nogo-66), MAG and/or TN-R (preferably TNR-EGFL) on neuronal cell adhesion in an in vitro assay. Following the identification of a peptide (or phage that displays a peptide) that is capable of blocking the inhibitory effects of Nogo (preferably Nogo-66), MAG and/or TN-R (preferably TNR-EGFL) on neuronal cell adhesion in an in vitro assay, the peptide is preferably formulated with one or more pharmaceutically acceptable ingredients for administration in vivo.

The invention further provides a method of searching for factors that are likely to reduce the inhibitory effect of TN-R, MAG and/or Nogo, the method comprising interrogating a sequence database to identify polypeptides, or nucleic acids that encode polypeptides, that comprise an amino acid sequence having at least 5 residues identical with corresponding residues in an amino acid sequence selected from the group consisting of:

| | |
|---|---|
| YLTQPQS; | (SEQ ID NO. 1) |
| GSLPHSL; | (SEQ ID NO. 2) |
| TQLFPPQ; | (SEQ ID NO. 3) |
| HSIPDNI; | (SEQ ID NO. 4) |
| HHMPHDK; | (SEQ ID NO. 5) |
| YTTPPSP; and | (SEQ ID NO. 6) |
| QLPLMPR. | (SEQ ID NO. 7) |

The database is preferably a cDNA database. It may be an EST database. Preferably it is a database of sequences expressed in mammalian CNS. Less specific databases may be used, although this may generate more false positive results.

The invention further provides a method of searching for factors that are likely to reduce the inhibitory effect of TN-R, MAG and/or Nogo, the method comprising screening a cDNA library with an oligonucleotide probe which is capable of hybridising under stringent conditions with a nucleic acid sequence that encodes an amino acid sequence having at least 5 residues identical with corresponding residues in an amino acid sequence selected from the group consisting of:

| | |
|---|---|
| YLTQPQS; | (SEQ ID NO. 1) |
| GSLPHSL; | (SEQ ID NO. 2) |
| TQLFPPQ; | (SEQ ID NO. 3) |
| HSIPDNI; | (SEQ ID NO. 4) |
| HHMPHDK; | (SEQ ID NO. 5) |
| YTTPPSP; and | (SEQ ID NO. 6) |
| QLPLMPR. | (SEQ ID NO. 7) |

The cDNA library is preferably mammalian, more preferably human. The library is preferably derived from CNS tissue.

Each of the two preceding methods preferably further includes a step, following the identification of a candidate polypeptide, or nucleic acid encoding the candidate polypeptide, of testing the polypeptide for the ability to reduce the inhibitory effect of TN-R, MAG and/or Nogo. Preferred further steps are as indicated above.

Second Aspect

In this aspect, the invention provides nucleic acid vector comprising nucleic acid encoding one or more polypeptide domains selected from the group consisting of:
(a) the N-terminal (NogoN) domain of Nogo-A;
(b) the extracellular loop (Nogo66) of Nogo-B (also present in Nogo-A and Nogo-C);
(c) the third to fifth immunoglobulin-like repeats of MAG; and
(d) the EGF-like domain of TN-R.

The TN-R EGF-L domain has been identified in Xiao et al. (1996) as being capable of inhibiting neurite outgrowth in vitro of a neuronal cell line and primary neurons.

The vector will include control sequences necessary for the expression of said nucleic acid in mammalian cells. Preferably the vector is a commercially available vaccine vector, into which said nucleic acid has been inserted. Suitable and preferred commercially available vaccine vectors include the pcDNA 3.1 family of vectors, especially pcDNA 3.1$^+$, and pVAX1 (all from Invitrogen, San Diego, Calif., US).

Usually the nucleic acid will be DNA.

Preferably the nucleic acid encodes at least two of the domains, more preferably at least three, more preferably it encodes all four. The nucleic acid may encode a plurality of copies of any one or more of the domains.

Where the nucleic acid encodes more than one domain, the domains are preferably expressed as a fusion polypeptide. Preferably the domains are separated from one another by flexible linkers (preferably poly-Ala linkers, e.g. Ala$_3$ linkers) to facilitate correct folding of the domains.

Of the proteins Nogo A, Nogo B, TN-R and/or MAG (and/or preferably Nogo-C), the vector is preferably capable of expressing substantially only the domains indicated. NogoN is a domain of the Nogo A isoform. Nogo 66 is a domain found in all three isoforms, Nogo-A, Nogo-B and Nogo-C. In particular, the vector is preferably incapable of expressing other epitope-containing portions of the proteins. Of the proteins Nogo A, Nogo B, TN-R and/or MAG (and/or preferably Nogo-C), the vector preferably expresses no more than 20%, more preferably no more than 15%, no more than 12%, no more than 10%, no more than 8%, no more than 6%, no more than 5%, no more than 4%, no more than 3%, no more than 2% or no more than 1% of the protein lying outside the domains listed above. This is particularly preferred for vectors containing a domain or domains of only one of the proteins.

The amino acid sequences of Nogo A, Nogo B, Nogo C, TN-R and MAG are available from GenBank, for example under the following accession numbers:

MAG-X05301 (GI 56611)
TN-R-Z67996 (GI 1261914)
Nogo B-AJ251384 (GI 9408097)
Nogo A-AF320999 (GI 11878297)
Nogo C-CAB99250 (GI 9408100)

The domains preferably have the amino acid sequences shown below, i.e. for domain (c), the 508 residue amino acid sequence of MAG (1-508); for domain (d), the 205 residue amino acid sequence of TNR (125-329); for domain (a), the 185 amino acid sequence of NogoN (1-185); and for domain (b), the 66 amino acid sequence of Nogo66 (823-888).

```
MAG (1-508)
                                                              (SEQ ID NO:8)
MIFLTTLPLF WIMISASRGG HWGAWMPSSI SAFEGTCVSI PCRFDFPDEL

RPAVVHGVWY FNSPYPKNYP PVVFKSRTQV VHESFQGRSR LLGDLGLRNC

TLLLSTLSPE LGGKYYFRGD LGGYNQYTFS EHSVLDIINT PNIVVPPEVV

AGTEVEVSCM VPDNCPELRP ELSWLGHEGL GEPTVLGRLR EDEGTWVQVS

LLHFVPTREA NGHRLGCQAA FPNTTLQFEG YASLDVKYPP VIVEMNSSVE

AIEGSHVSLL CGADSNPPPL LTWMRDGMVL REAVAESLYL DLEEVTPAED

GIYACLAENA YGQDNRTVEL SVMYAPWKPT VNGTVVAVEG ETVSILCSTQ

SNPDPILTIF KEKQILATVI YESQLQLELP AVTPEDDGEY WCVAENQYGQ

RATAFNLSVE FAPIILLESH CAAARDTVQC LCVVKSNPEP SVAFELPSRN

VTVNETEREF VYSERSGLLL TSILTLRGQA QAPPRVICTS RNLYGTQSLE

LPFQGAHR

TNR (125-329)
                                                              (SEQ ID NO:9)
     CPCASS AQVLQELLSR IEMLEREVSV LRDQCNANCC QESAATGQLD

YIPHCSGHGN FSFESCGCIC NEGWFGKNCS EPYCPLGCSS RGVCVDGQCI

CDSEYSGDDC SELRCPTDCS SRGLCVDGEC VCEEPYTGED CRELRCPGDC

SGKGRCANGT CLCEEGYVGE DCGQRQCLNA CSGRGQCEEG LCVCEEGYQG

PDCSAVAPP

NogoN (1-185)
                                                              (SEQ ID NO:10)
MEDLDQSPLV SSSDSPPRPQ PAFKYQFVRE PEDEEEEEEE EEDEDEDLE

ELEVLERKPA AGLSAAPVPT APAAGAPLMD FGNDFVPPAP RGPLPAAPPV

APERQPSWDP SPVSSTVPAP SPLSAAAVSP SKLPEDDEPP ARPPPPPPAS

VSPQAEPVWT PPAPAPAAPP STPAAPKRRG SSGSV

Nogo66 (823-888)
                                                              (SEQ ID NO:11)
    RIYKGVIQ AIQKSDEGHP FRAYLESEVA ISEELVQKYS NSALGHVNCT

IKELRRLFLV DDLVDSLK
```

The vector preferably encodes a polypeptide having the amino acid sequence MAG(1-508)-Ala$_n$-TNR(125-329)-Ala$_n$-NogoN(1-185)-Ala$_n$-Nogo66(823-888) (SEQ ID NO:12), where Ala$_n$ represents an polyalanine linker. n is preferably 3.

The domains are preferably encoded by the following sequences, i.e. for domain (c), the 508 codon nucleic acid sequence of MAG (126-1649); for domain (d), the 205 codon nucleic acid sequence of TNR (454-1068); for domain (a), the 185 codon nucleic acid sequence of NogoN (1-555); and/or for domain (b), the 66 codon nucleic acid sequence of Nogo66 (2467-2664):

MAG (126-1649)

(SEQ ID NO:13)

```
atgat attccttacc accctgcctc tgttttggat aatgatttca
gcttctcgag gggggcactg gggtgcctgg atgccctcgt ccatctcagc
cttcgagggc acgtgtgtct ccatccctg ccgtttcgac ttcccggatg
agctcagacc ggctgtggta catggcgtct ggtatttcaa cagtccctac
cccaagaact acccgccagt ggtcttcaag tcccgcacac aagtggtcca
cgagagcttc cagggccgta gccgcctgtt gggagacctg ggcctacgaa
actgcaccct gcttctcagc acgctgagcc ctgagctggg agggaaatac
tatttccgag gtgacctggg cggctacaac cagtacacct tctcggagca
cagcgtcctg gacatcatca acaccccaa catcgtggtg ccccagaag
tggtggcagg aacggaagta gaggtcagct gcatggtgcc ggacaactgc
ccagagctgc gccctgagct gagctggctg ggccacgagg gctaggga
gcccactgtt ctgggtcggc tgcgggagga tgaaggcacc tgggtgcagg
tgtcactgct acacttcgtg cctactagag aggccaacgg ccaccgtctg
ggctgtcagg ctgccttccc caacaccacc ttgcagttcg agggttacgc
cagtctggac gtcaagtacc ccccggtgat tgtggagatg aattcctctg
tggaggccat tgagggctcc cacgtcagcc tgctctgtgg ggctgacagc
aacccgccac cgctgctgac ttggatgcgg gatgggatgg tgttgaggga
ggcagttgct gagagcctgt acctggatct ggaggaggtg accccagcag
aggacggcat ctatgcttgc ctggcagaga tgcctatgg ccaggacaac
cgcacggtgg agctgagcgt catgtatgca ccttggaagc ccacagtgaa
tgggacggtg gtggcggtag aggggagac agtctccatc ctgtgttcca
cacagagcaa cccggaccct attctcacca tcttcaagga gaagcagatc
ctggccacgg tcatctatga gagtcagctg cagctggaac tccctgcagt
gacgcccgag gacgatgggg agtactggtg tgtagctgag aaccagtatg
gccagagagc caccgccttc aacctgtctg tggagtttgc tcccataatc
cttctggaat cgcactgtgc agcggccaga gacaccgtgc agtgcctgtg
tgtggtaaaa tccaaccgg aaccctccgt ggcctttgag ctgccttccc
gcaacgtgac tgtgaacgag acagagaggg agtttgtgta ctcagagcgc
agcggcctcc tgctcaccag catcctcacg ctccggggtc aggcccaagc
cccaccccgc gtcatttgta cctccaggaa cctctacggc acccagagcc
tcgagctgcc tttccaggga gcacccga
```

This sequence commences with a start codon; if any other sequence is used at the 5' end of the nucleic acid, a start codon will be required. It is of course a matter of routine to engineer this into any nucleic acid sequence of interest, though it will be noted that Nogo(1-555) also commences with a start codon.

It is, however, thought that fragments, derivatives or variants of these specific domains will also give rise to effective vaccines. Accordingly, a polypeptide domain within the meaning of the invention may be a fragment of any one of the four amino acid sequences given above, the fragment preferably consisting of at least 15 contiguous amino acids from

```
TNR (454-1068)
                                                         (SEQ ID NO:14)
   tgtccat gtgccagttc agcccaggtg ctgcaggagc tgctgagccg gatcgagatg ctggagaggg aggtgtcggt gctgcgagac cagtgcaacg ccaactgctg ccaagaaagt gctgccacag dacaactgga ctatatccct cactgcagtg gccacggcaa ctttagcttt gagtcctgtg gctgcatctg caacgaaggc tggtttggca agaattgctc ggagccctac tgcccgctgg gttgctccag ccgggggtg tgtgtggatg ccagtgcat ctgtgacagc gaatacagcg gggatgactg ttccgaactc cggtgcccaa cagactgcag ctcccggggg ctctgcgtgg acggggagtg tgtctgtgaa gagccctaca ctggcgagga ctgcagggaa ctgaggtgcc ctggggactg ttcggggaag gggagatgtg ccaacggtac ctgtttatgc gaggagggct acgttggtga ggactgcggc cagcggcagt gtctgaatgc ctgcagtggg cgaggacaat gtgaggaggg gctctgcgtc tgtgaagagg gctaccaggg ccctgactgc tcagcagttg cccctcca NogoN (1-555)
                                                         (SEQ ID NO:15)
atggaagacc tggaccagtc tcctctggtc tcgtcctcgg acagcccacc ccggccgcag cccgcgttca agtaccagtt cgtgagggag cccgaggacg aggaggaaga agaggaggag gaagaggagg acgaggacga agacctggag gagctggagg tgctggagag gaagcccgcc gccgggctgt ccgcggcccc agtgcccacc gcccctgccg ccggcgcgcc cctgatggac ttcggaaatg acttcgtgcc gccggcgccc cggggacccc tgccggccgc tcccccgtc gccccggagc ggcagccgtc ttgggacccg agcccggtgt cgtcgaccgt gcccgcgcca tccccgctgt ctgctgccgc agtctcgccc tccaagctcc ctgaggacga cgagcctccg gcccggcctc ccctcctcc cccggccagc gtgagccccc aggcagagcc cgtgtggacc ccgccagccc cggctcccgc cgcgccccc tccaccccgg ccgcgcccaa gcgcagggc tcctcgggct cagtg Nogo66 (2467-2664)
                                                         (SEQ ID NO:16)
    agga tatacaaggg tgtgatccaa gctatccaga aatcagatga aggccaccca ttcagggcat atctggaatc tgaagttgct atatctgagg agttggttca gaagtacagt aattctgctc ttggtcatgt gaactgcacg ataaaggaac tcaggcgcct cttcttagtt gatgatttag ttgattctct gaag
``` said sequence, more preferably at least 17, more preferably at least 20, 25, 30, 40, 50 or 60 amino acids. For MAG, NogoN and TNR, the size of the fragment is more preferably at least 80 amino acids, more preferably 100, 120, 140, 160 or 180 amino acids. For TNR and MAG, the length is more preferably 200 amino acids. For MAG, the length is more preferably 250, 300, 350, 400 or 450 amino acids. The fragment will include one or more epitopes of the specific domain whose sequence is given above, and will retain the ability of the domain to raise an antibody response in vivo. Thus, the fragment will be capable of raising antibodies in vivo that cross-react with the corresponding domain. Linear epitope mapping is a matter of routine for the skilled person.

Similarly, a polypeptide domain within the meaning of the invention may be a variant of any one amino acid sequence (the reference amino acid sequence) given above. In this context, a variant is a polypeptide having a sequence which differs from the reference amino acid sequence, but which includes a portion of at least 15 amino acids that has at least 65% amino acid identity to a corresponding portion of the reference sequence. Preferably the level of identity is at least 70%, 75%, 80%, 85%, 90%, 95%, 98% or 99%. Preferably the portion is at least 17 amino acids in length, more preferred lengths are those given in the preceding paragraph for the lengths of fragments. Again, the variant will generally include one or more epitopes of the specific domain whose sequence is given above, and will retain the ability of the domain to raise an antibody response in vivo. Thus, the variant will be capable of raising antibodies in vivo that cross-react with the corresponding domain.

The invention also provides a composition comprising the vector of the invention, formulated together with one or more pharmaceutically acceptable ingredients for use as a (therapeutic) vaccine. Preferably the composition is formulated for administration by injection.

The invention further provides the vector of the invention, for use in a method of treatment. The treatment may be of CNS damage, especially SCI or stroke.

The invention also provides the use of the vector of the invention in the manufacture of a medicament for the treatment of CNS damage, especially SCI and stroke.

The invention also provides a method for treating CNS damage in a patient, the method comprising administering a vector of the invention to the patient as a therapeutic vaccine.

The vectors of the invention will typically be administered by injection, although other vaccine delivery methods are known in the art (such as oral or transdermal delivery and "needle-free" injection) and may be used in accordance with the invention. Injection will typically be intra-muscular. While the blood-brain barrier normally provides an obstacle to the passage of antibodies, CNS damage (especially injury, e.g. external injury) will generally allow passage of antibodies across the blood-brain barrier at the site of damage. It is considered therefore that no special measures are required to allow passage across the blood-brain barrier of antibodies raised in response to vaccination with the vector of the invention.

The invention further provides a polypeptide consisting essentially of one or more polypeptide domains selected from the group consisting of:
 (a) the N-terminal (NogoN) domain of Nogo-A;
 (b) the extracellular loop of Nogo-B (also present in Nogo-A and Nogo-C);
 (c) the third to fifth immunoglobulin-like repeats of MAG; and
 (d) the EGF-like domain of TN-R.

Preferred features of the polypeptide are as defined above for the polypeptide encoded by the vector.

The invention also provides a composition comprising the polypeptide of the invention, formulated together with one or more pharmaceutically acceptable ingredients for use as a (therapeutic) vaccine. Preferably the composition is formulated for administration by injection.

The invention further provides the polypeptide of the invention, for use in a method of treatment. The treatment may be of CNS damage, especially SCI or stroke.

The invention also provides the use of the polypeptide of the invention in the manufacture of a medicament for the treatment of CNS damage, especially SCI or stroke.

The invention also provides a method for treating CNS damage in a patient, the method comprising administering a polypeptide of the invention to the patient as a therapeutic vaccine.

Administration is preferably as described for the vector.

The invention further provides analogous methods and uses of antibodies capable of specifically binding to any one domains (a)-(d), or preferably mixtures of antibodies together capable of binding two, three or all four of domains (a)-(d) for the treatment of CNS damage, especially SCI or stroke. The antibodies will be administered directly to the patient (preferably as for the peptides of the first aspect, e.g. by direct injection into the CNS, into the site of damage or into the cerebro-spinal fluid), instead of administering a nucleic acid or polypeptide vaccine to generate an antibody response. Antibody fragments capable of specific binding are regarded to be antibodies for this purpose.

DETAILED DESCRIPTION

Peptides

The term "peptide" is intended to refer to a molecule consisting of several amino acids, adjacent pairs of amino acids being linked by peptide bonds. A peptide bond has the structure —CO—NH—. Amino acids may be naturally occurring or non-naturally occurring. Terminal amino acids may include terminal modifications. Naturally occurring chiral amino acids (i.e. amino acids other than non-chiral glycine) are of the L-isoform. Peptides of the invention, however, may include or consist of amino acids of the D-isoform. Such D-amino acids may be the D-isoforms of naturally occurring L-amino acids, or may have no naturally occurring L-isoform. The inclusion of D-amino acids in the peptides of the invention may assist in reducing clearance of the peptide in vivo.

Synthesis of Peptides

Peptides may be generated wholly or partly by chemical synthesis. The peptides of the invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Phage Display

Phage display is a recent and promising technique in biomolecular engineering which can survey tens of millions of short peptides for tight binding to an antibody receptor or other binding protein. Phage display was firstly described in 1985 (Smith et al, 1985) and is a selection technique in which a peptide or protein is expressed as a fusion with a coat protein of a bacteriophage, resulting in display of the fused protein on the surface of the virion, while the DNA encoding the fusion resides within the virion. Phage display creates a physical linkage between a vast library of random peptide sequences and DNA encoding each sequence, allowing rapid identification of peptide ligands for a variety of target molecules by an in vitro selection process called panning (Scott et al, 1990; Arap et al 1998).

Interactions that involve particular protein domains (either protein/protein or protein/non-protein interactions) typically only need 8-12 amino acids, among which 5-8 amino acids play a key role. Phage display libraries displaying peptides of 6-10 amino acid residues have been successfully used in a number of applications, including epitope mapping, mapping protein-protein contacts, identification of peptide mimetics of non-peptide ligands and design of novel vaccine and new drugs (Scott et al, 1990; Cwirla et al, 1990; Devlin et al 1990 Felici et al, 1991; Motti et al, 1994; Hong et al, 1995; Arap et al, 1998; Nilsson et al, 2000).

Recent work has shown that a series of peptides isolated using a broad range of enzymes as targets contained similar amino acid sequences for each target and bound one or two sites per target by competition analysis. Of 17 peptides tested, 13 were found to be specific inhibitors of enzyme function. Peptidic surrogate ligands identified using phage display are preferentially targeted to a limited number of sites that inhibit enzyme function (Hyde-DeRuyscher et al 2000).

Mimetics

Non-peptide "small molecules" are often preferred to peptides for in vivo pharmaceutical use. Accordingly, mimetics of the peptides of the invention may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of peptide are commonly used to refine such peptide motifs. These parts or residues constituting the active region of the compound are known as its "pharmacophore".

Once the pharmacophore has been found, its structure is modelled according to its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

Sequence Identity

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Stringent Conditions

Stringent conditions may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example 50% (v/v) formamide with 0.1% bovine serum albumin/0.1% Ficoll/0.1% polyvinylpyrrolidone/50 mM sodium phosphate buffer at pH 6.5 with 760 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The Subject

The subject to which the compositions and/or treatments of the invention will be administered will be a mammal, preferably an experimental animal such,as a rodent (e.g. a rabbit, rat or mouse), dog, cat, monkey or ape, or a farm animal such as a cow, horse, sheep, pig or goat. More preferably, the subject is human.

Generally, the subject will have CNS damage, usually CNS injury, e.g. a head injury. More preferably, however, the damage is to the spinal cord, e.g. SCI. In experimental animals, the damage may be experimental. The CNS damage may also result from a disease or disorder, e.g. epilepsy, stroke, or a neurodegenerative condition, learning memory-related condition and/or dementia such as Alzheimer's disease or Parkinson's disease.

The treatments of the invention will generally be intended for use in conjunction with other therapies, such as surgery and/or rehabilitation.

Formulations

It is preferable to present the peptides, mimetics, and vectors of the invention as pharmaceutical formulations (e.g., composition, preparation, medicament) comprising at least one active compound, as defined above, together with one or more other pharmaceutically acceptable ingredients well known to those skilled in the art, including, but not limited to, pharmaceutically acceptable carriers, adjuvants, excipients, buffers, preservatives and stabilisers. The formulation may further comprise other active agents.

Thus, the present invention further provides a method of making a pharmaceutical composition as previously defined, the method comprising admixing at least one peptide or vector of the invention together with one or more pharmaceutically acceptable ingredients well known to those skilled in the art, e.g., carriers, adjuvants, excipients, etc.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example Remington's Pharmaceutical Sciences, 20th Edition, 2000, pub. Lippincott, Williams & Wilkins; and Handbook of Pharmaceutical Excipients, 2nd edition, 1994.

Formulations may suitably be injectable formulations, e.g. in the form of aqueous, isotonic, pyrogen-free, sterile solutions, in which the active compound is dissolved. Such liquids may additional contain other pharmaceutically acceptable ingredients, such as anti-oxidants, buffers, preservatives, stabilisers, bacteriostats, suspending agents, thickening agents, and solutes which render the formulation isotonic with the blood or cerebrospinal fluid. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Administration

Administration of the peptides of the invention will generally be by injection, preferably directly into the CNS. Injection may be directly into the site of damage, e.g. into the site of damage. Alternatively, injection may be into the cerebrospinal fluid, typically near the site of injury.

Experimental work underlying the invention and embodiments of the invention will now be described, by way of example only, with reference to the accompanying FIG. 1, which shows the primers used to isolate the inhibitory domains from the proteins MAG, TN-R and Nogo. Coding sequence (or the complementary strand) is shown in bold. Start (Met) and stop (***) codons are doubly underlined. Restriction sites are underlined. SEQ ID NOS are as follows:

| Primer | SEQ ID NO |
|---|---|
| MAG1 | 17 |
| MAG2 | 18 |
| TNR1 | 19 |
| TNR2 | 20 |
| NogoN1 | 21 |
| NogoN2 | 22 |
| Nogo66-1 | 23 |
| Nogo66-2 | 24 |

Also shown schematically is the resultant construct (SEQ ID NO:25) obtained by digestion and sequential connection of the resultant PCR products. Restriction sites are underlined. Ala-encoding codons are labelled. Coding sequence for each inhibitory domain is represented by the bracketed name of the domain. The stop codon is labelled ***.

ASPECT 1, EXAMPLE 1

Identification of Nogo Domains Responsible having Inhibitory Properties

Repulsion Assay

NG108 cells (mouse neuroblastoma—rat glioma hybrid cells, commercially available from the American Tissue Type Culture Collection, Manassas, Va., USA, under accession number ATCC HB-12317) were plated on coated substrates using Nogol-25, Nogol-50, Nogol-66 and GST-Nogo-66 as well as GST as control. Generation and purification of the recombinant domains of Nogo, either alone or as fusion proteins with GST, were performed as previously described (Xiao Z C et al, 1996).

NG108 cells were repelled significantly from Nogol-50, Nogol-66, and GST-Nogo-66, but not Nogol-25 and GST.

Neurite Outgrowth Assay

NG108 cells were plated on coated substrates using Nogol-25, Nogol-50, Nogol-66, and GST-Nogo-66 as well as GST as control.

Neurite outgrowth of NG108 cells were inhibited significantly from Nogol-50, Nogol-66, and GST Nogo-66, but not Nogol-25 and GST.

ASPECT 1, EXAMPLE 2

Screening of Novel Short Peptides Against Neuronal Growth Inhibitory Molecules TN-R, MAG, and Nogo through Phage Display Technology Purification of TN-R, MAG and Nogo from adult mouse brains was performed by immumoaffinity chromatography as previously described (Pesheva, P et al, 1989). Generation and purification of the recombinant domains of TN-R, MAG, Nogo as fusion proteins with GST were performed as previously described (Xiao Z C et al, 1996). All these proteins were used as phage binding targets for rapid screening, using the Ph. D-7TM phage display peptide library kit (New England Biolabs, Ltd) according to the manufacturer's instructions.

Briefly, a library of phages, displaying different peptide sequences, was exposed to a plate coated with the target protein. Unbound phage was washed away and specifically bound phage was eluted by lowering pH. The eluted pool of phage was amplified, and the process was repeated 3-4 times.

After 3-4 rounds of affinity selection, several specific phage clones were isolated from 7-mer random peptide phage-displayed libraries and identified by ELISA. The peptide-encoding sequences of the specific phage clones were determined by automated sequencing. The sequences of peptides which bound specifically to the targeted proteins were obtained.

The framework sequence of the phage coat protein, into which a 7-mer peptide-encoding sequence is inserted in each phage, is as follows:

(SEQ ID NO:26)
TTA TTC GCA ATT CCT TTA GTG GTA CCT TTC TAT TCT CAC TCT (SEQ ID NO:27)
GGT GGA GGT TCG GCC GAA ACT GTT GAA AGT TGT

. . . represents the site of insertion of the 7-mer peptide-encoding sequence. A Kpn1 site is underlined, a Eag1 site is doubly underlined.

Exemplary 7-mer peptide-endcoding sequences are shown below. "n" refers to the number of isolated phages displaying a peptide having the sequence shown (though there was of course some variability in the encoding nucleic acid sequences, owing to the degeneracy of the genetic code). "SIN" is an abbreviation for "SEQ ID NO." and refers to the peptide sequence. The SEQ ID NOS of the nucleic acid sequences from the top to the bottom of the table are as follows: SEQ ID NO: 28, SEQ ID NO: 29, SEQ ID NO: 30, SEQ ID NO: 31, SEQ ID NO: 32, SEQ ID NO: 29, SEQ ID NO: 33. SEQ ID NO: 28, SEQ ID NO: 34, SEQ ID NO: 35.

| Target | Exemplary nucleic acid | Peptide | SIN |
| --- | --- | --- | --- |
| Nogo-66 | TAT CTG ACG CAG CCT CAG TCG | YLTQPQS (n = 43) | 1 |
| Nogo-66 | GGT TCT CTG CCT CAT TCG CTG | GSLPHSL (n = 8) | 2 |
| TNR-EGFL | ACG CAG CTG TTT CCT CCT TAG | TQLFPPQ (n = 18) | 3 |
| TNR-EGFL | CAT TCT ATT CCT GAT AAT ATT | HSIPDNI (n = 3) | 4 |
| TNR-EGFL | CAT CAT ATG CCT CAT GAT AAG | HHMPHDK (n = 1) | 5 |
| TNR-EGFL | GGT TCT CTG CCT CAT TCG CTG | GSLPHSL (n = 1) | 2 |
| TNR-EGFL | TAT ACG ACG CCT CCG AGT CCT | YTTPPSP (n = 1) | 6 |
| MAG | TAT CTG ACG CAG CCT CAG TCG | YLTQPQS (n = 19) | 1 |
| MAG | CAG CTT CCG CTT ATG CCT CGT | QLPLMPR (n = 5) | 7 |
| MAG | ACG CAG CTG TTT CCT CCT CAG | TQLFPPQ (n = 7) | 3 |

ASPECT 1, EXAMPLE 3

In Vitro Assay for Phages Displaying Peptides that Reduce the Inhibitory Effect of Nogo, MAG and TN-R on Neuronal Adhesion Tissue culture petri dishes (Becton Dickinson) with a diameter of 3.5 cm were coated with methanol-solubilized nitrocellulose according to Lagenaur and Lemmon (1987) and air-dried under a sterile hood. Then the petri dishes were incubated with PBS containing 5 µg/ml poly-DL-ornithine for 2 hours at 37° C. Subsequently, the dishes were washed three times with PBS and dried under a sterile hood.

Protein spots (1.5 µl of 5 µM GST, 5 µM GST-Nogo66, 100 µM Nogo66, 100 µM Nogo1-50 or 100 µM Nogo1-25) were applied to the nitrocellulose-coated surfaces of the petri dishes and incubated for 2 hours at 37° C. in a humidified atmosphere. Subsequently, the spots were washed three times with PBS. The dishes were then flooded with PBS containing 2% heat-inactivated fatty acid-free BSA (Sigma) and incubated overnight to block residual non-specific protein binding sites.

Then, the dishes were washed with PBS and NG108 cells were plated in 2 ml of Dulbecco's modified Eagle's medium containing 10% fetal bovine serum at a density of $2.5 \times 10^5$ cells/ml and incubated at 37° C. in a humidified atmosphere. After 12 hours, the dishes were gently washed three times with PBS and the cells fixed by flooding with PBS containing 2.5% glutaraldehyde. After fixation, cultures were stained with 0.5% toluidine blue (Sigma) in 2.5% sodium carbonate. The stained cultures were then washed three times with water and air-dried.

Cells adhering to the various spots were photographed and counted. All experiments were performed at least three times. Statistical analysis was carried out by Student test. The level of significance was chosen as $p<0.05$.

GST-Nogo66, Nogo66 and Nogo1-50 all displayed significantly reduced NG108 cell counts compared to GST; Nogo1-25 did not.

NG108 cells were plated on poly-DL-ornithine-treated tissue culture petri dish as single-cell suspensions. Specific phages that display the Nogo66-, MAG- and TNR-binding peptides identified above were added to the cell culture. Cells were maintained for 24 hours before fixation and staining with toluidine blue. Cell adhesion was determined as previously described.

Phage displaying the peptide YLTQPQS (SEQ ID NO. 1) was able to block the inhibitory effects of Nogo-66 and MAG on NG108 cell binding; phage displaying the peptide TQLFPPQ (SEQ ID NO. 3) was able to block the inhibitory effect of TNR-EGFL on NG108 cell binding.

ASPECT 1, EXAMPLE 4

In Vitro Assay for Peptides that Reduce the Inhibitory Effect of Nogo, MAG and TN-R on Neuronal Adhesion All the screened consensus peptides are synthesized using the solid-phase method by means of a Peptide Synthesizer Model 1000. Neurite outgrowth and growth cone repulsion assays are performed as described previously (Xiao Z C et al, 1997). Purified intact TN-R, MAG and Nogo and recombinant domains of TN-R, MAG and Nogo are be coated as substrate, to allow identification of the inhibitory domains of TN-R, MAG and Nogo. In a further assay, the synthesized peptides are mixed with the relevant protein/domain before coating, to identify peptides that can neutralize the inhibitory effects of TN-R, MAG and/or Nogo in vitro.

ASPECT 1, EXAMPLE 5

In Vivo Test for Peptides that can Alleviate Spinal Cord Injury

Those consensus short peptides that can neutralize the inhibitory effects of TN-R, MAG and/or Nogo in vitro are used in vivo to determine that they alleviate spinal cord injury (Bregman et al, 1995). These peptides are injected into spinal cord injured adult rat. Regeneration of axons is assayed by immunohistochemistry by comparison with an untreated control. Function improvement is also analyzed.

ASPECT 1, EXAMPLE 6

Screening for Candidate Factors that can Abolish the Inhibitory Effects of TN-R, MAG, and/or Nogo Degenerate oligonucleotide sequences are determined for the peptides that can neutralize the inhibitory effects of TN-R, MAG and/or Nogo in vitro and/or in vivo (preferably both). EST databases (preferably databases of CNS-derived ESTs) are searched using the degenerate oligonucleotide sequences. CNS cDNA libraries are screened using labelled degenerate oligonucleotide probes. Hits represent candidate factors that can abolish the inhibitory effects of TN-R, MAG and/or Nogo. These candidate factors are purified as GST-fusion protein, and the neutralizing effects are tested as described previously for the peptides.

An alternative way to test the neutralizing effects in vivo is to transplant candidate factor-transfected neurons to the injured spinal cord in an experimental animal and observe the neutralizing results.

New factors that can abolish the inhibitory effects of TN-R, MAG and/or Nogo are therefore obtained, and are useful for treating, or in the development of treatments for, CNS damage, especially spinal injury.

ASPECT 2, EXAMPLE 1

Vector Construction

Nucleic acid encoding the following domains was obtained by PCR: N-terminal and 66-Aa extracellular domain of Nogo-A, third to fifth Ig like domain of MAG and the EGF like domain of human TNR.

PCR primers were designed to include restriction enzyme sites and to encode Ala linkers at the ends of the subcloned sequences (see FIG. 1). Therefore, when the PCR products were double digested by restriction enzymes and then connected sequentially, DNA encoding the Ala linkers was located between each pair of neighbouring domains (again, see FIG. 1). The Ala linkers facilitate proper folding of the domains.

Then, the sequentially connected DNA was double digested by BamH I and XbaI and then inserted into a pcDNA 3.1 vector (Invitrogen) to produce a recombinant vector. The recombinant vector was verified by agarose gel and sequence analysis.

ASPECT 2, EXAMPLE 2

Verification of the Inhibitory Functions of the Recombinant Vector In Vitro

Before the DNA vaccine can be injected into test animals, in vitro testing must be carried out to make sure that the vaccine can be expressed by mammalian cells and can be secreted out of the cell to stimulate the immune system of the host.

To check this, COS-1 cells were transfected with the recombinant vector. After transient expression, the cells and the medium were collected respectively and Western-Blot was performed using antibodies to the inhibitory molecules (Xiao et al, 1996) to verify that the recombinant protein is secreted out the cell and can act as an antigen to stimulate the host immune system when the vector is administered in vivo as a vaccine.

Transfected cells were detected positive for MAG and TNR antibodies compared to non-transfected cells. Immunoreactivity for Nogo was detected in both transfected and non-transfected cells.

48 hours after transient transfection with the recombinant plasmid, the medium was collected and immunoprecipitated with anti-NogoN or anti-TNR-EGFL antibody using protein A-agarose. The precipitates were separated by 10% and 6% SDS-PAGE and probed for Nogo and TNR, respectively. Each precipitate revealed immunoreactivity for the corresponding antibody, indicating that the protein is being secreted.

ASPECT 2, EXAMPLE 3

Dot-blot of GST Fusion Proteins with Pre-immune Sera and Anti-sera

Anti-sera were collected from Lewis rats after 2-month vaccination with recombinant plasmid. A serial concentration of GST-Nogo66, GST-NogoN, GST-TNR/EGFL, GST-MAG Ig3-5 and GST were dotted as substrates and subsequently blotted with sera. Anti-sera specially recognized GST fusion proteins, but not GST. Pre-immune sera recognised neither the fusion proteins, nor GST.

ASPECT 2, EXAMPLE 4

Trial of the Recombinant Vector as a DNA Vaccine

To check the regeneration of the injured spinal cord after immunization with the DNA vaccine, the recombinant DNA vector is injected into a test animal. The anti-serum of immunized animals is assayed to verify the immune response after the injection of DNA vaccine.

A semi-transected model for spinal cord injury is used. After a period of time, a morphological study of the injured spinal cord neuron/axon, and a behavioral study of the animals is performed.

(1) Immunization and Spinal Cord Lesioning 6 week-old female Lewis rats are immunized once weekly with 100 µg of recombinant vector from the preceding examples. pcDNA3.1 vector lacking the insertion is used as a control. The vector is injected into the back of the rat. After the rats have produced anti-serum, the spinal cords are lesioned. The rats continue to receive twice monthly immunizations for another 6 weeks.

The rats are anesthetized with Somnitol (1 mg/20 g body weight), and a lower thoracic laminectomy is done (T9). The dorsal half of the spinal cord is then cut with a pair of microscissors to sever the corticospinal tracts. The depth of each lesion, about 1 mm, is estimated by a mark placed on the tip of the micro-scissors. After a 6 week survival period post lesion, the rats are anesthetized and a 5% solution of WGA-HRP (wheat germ agglutinin-horseradish peroxidase) is injected onto the sensory-motor cortex as described (Li et al., 1996). 48 hours after injection of WGA-HRP, the animals are sacrificed by intracardiac perfusion, and the longitudinal cryostat section of the spinal cord is reacted for HRP histochemistry as described (Li et al., 1996).

(2) Verification of the Immuno-Response of the Immunized Animals

To verify that the antisera of the immunized animals have the function of blocking the inhibitory effect of the inhibitory domains on neurite outgrowth, a neurite growth assay is used to test the serum of the immunized animals. A 4-well dish is first coated with solubilized nitrocellulose and preincubated with 5 µg/ml poly-L-lysine. The GST fusion inhibitory domains or peptides are placed in the well as a 2 µl drop and then incubated for 4 hrs at 37° C. These wells are then incubated overnight at 4° C. with the serum from either control mice or mice immunized with the DNA vaccine. The serum is removed, and postnatal day 10 rat cerebellar neurons purified by Percoll density gradient centrifugation are plated at a density of 1×10⁶ cells per well. The cells are cultured in serum-free chemically defined medium for 24 hrs, fixed with 4% paraformaldehyde, and stained with Coomassie blue. Neurite length is measured using a Universal Image I image analysis system. Data is analyzed using the Student-Newman-Keul's test to determine statistically significant differences (Li et. al., 1996).

(3) Morphological Study of the Injured Spinal Cord

To check the regeneration of the transected axon, the rats are perfused with 4% paraformaldehyde, and a 10 µm thick longitudinal cryostat section of the spinal cord is picked up on gelatin-coated glass slides. The sections are incubated with a biotinylated goat anti-rat antibody overnight and then with streptavidin-conjugated fluorescein for 1 hr, to detect circulating antibodies.

(4) Functional Testing of the Animals

The functional recovery of the experimental rat is also carried out. Contact placing response is tested by lightly touching the dorsal aspect of the hind limb without causing joint displacement. The ability of the animals to lift the foot and place it onto the support surface is then assessed in three to six repetitions. Greater than a 30% response will be scored as positive (Kukel-Bagden et. al., 1993).

(5) Safety Testing

The safety of this vaccination approach is assessed by administering the vaccine to test animals (unlesioned and lesioned) and looking for adverse events, especially loss of sensory or motor function and behavioral or cognitive impairments.

CNS tissue is examined histologically to look for autoimmune damage, e.g. by immunostaining using monoclonal anti-CNPase (Sigma C5922, lot 71k4889). CNPase is a protein expressed by oligodendrocytes, 2',3'-cyclic nucleotide 3'-phosphodiesterase.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

All documents cited herein are incorporated by reference in their entirety and for all purposes.

REFERENCES

Ajemian A, Ness R, David S. Tenascin in the injured rat optic nerve and in non-neuronal cells in vitro: potential role in neural repair. J Comp Neurol. 1994 Feb. 8: 340(2): 233-42

Altschul S F, Gish W. Local alignment statistics. Methods Enzymol 1996;266:460-80.

Arap W, Pasqualini R, Ruoslahti. Cancer treatment by targeted drug delivery to tumor vasculature in a mouse model. Science 1998 Jan. 16;279(5349):377-80.

Becker C G, Becker T, Meyer R L, Schachner M. Tenascin-R inhibits the growth of optic fibers in vitro but is rapidly eliminated during nerve regeneration in the salamander Pleurodeles waltl.: J Neurosci 1999 Jan. 15;19(2):813-27.

Becker T, Anliker B, Becker C G, Taylor J, Schachner M, Meyer R L, Bartsch U. Tenascin-R inhibits regrowth of optic fibers in vitro and persists in the optic nerve of mice after injury. Glia 2000 Feb. 15;29(4):330-46.

Bregman B S, Kunkel-Bagden E, Schnell L, Dai H N, Gao D, Schwab M E. Recovery from spinal cord injury mediated by antibodies to neurite growth inhibitors. Nature 1995 Nov. 30;378(6556):498-501.

Chen M S, Huber A B, Van der Haar M E, Frank M, Schnell L, Spillmann A A, Christ F, Schwab M E. Nogo-A is a myelin-associated neurite outgrowth inhibitor and an antigen for monoclonal antibody IN-1. Nature. 2000 Jan. 27; 403(6768):434-9

Chiquet-Ehrismann R, Tannheimer M, Koch M, Brunner A, Spring J, Martin D, Baumgartner S, Chiquet M. Tenascin-C expression by fibroblasts is elevated in stressed collagen gels. J Cell Biol 1994 December;127(6 Pt 2):2093-101.

Collins B E, Yang J S, Mukhopadhyay G, Filbin M T, Kiso M, Hasegawa A, Schnaar R L. Sialic acid specificity of myelin-associated glycoprotein binding. J Biol Chem. 1997 Jan. 10; 272(2): 1248-55

Cwirla S E, Peters E A, Barrett R W, Dower W J. Peptides on phage: a vast library of peptides for identifying ligands. Proc Natl Acad Sci USA 1990 August;87(16):6378-82.

DeBellard M E, Tang S, Mukhopadhyay G, Shen Y J, Filbin M T. Myelin-associated glycoprotein inhibits axonal regeneration from a variety of neurons via interaction with a sialoglycoprotein. Mol Cell Neurosci 1996 February;7 (2):89-101.

Deckner M, Lindholm T, Cullheim S, Risling M. Differential expression of tenascin-C, tenascin-R, tenascin/J1, and tenascin-X in spinal cord scar tissue and in the olfactory system. Exp Neurol 2000 December;166(2):350-62.

Devlin J J, Panganiban L C, Devlin P E. Random peptide libraries: a source of specific protein binding molecules. Science 1990 Jul. 27;249(4967):404-6.

Erickson H P. Tenascin-C, tenascin-R and tenascin-X: a family of talented proteins in search of functions. Curr Opin Cell Biol. 1993 October;5(5):869-76. Review.

Felici F, Castagnoli L, Musacchio A, Jappelli R, Cesareni G. Selection of antibody ligands from a large library of oligopeptides expressed on a multivalent exposition vector. J Mol Biol 1991 Nov. 20;222(2):301-10.

Filbin, M T. Myelin-associated inhibitors of axonal regeneration in the adult mammalian CNS. Nature Reviews (Neuroscience). September 2003; Vol. 4: 1-11

Fournier A E, Grandpre T, Strittmatter S M. Identification of a receptor mediating Nogo-66 inhibition of axonal regeneration. Nature. 2001 Jan. 18; 409: 341-46

Fuss B, Pott U, Fischer P, Schwab M E, Schachner M. Identification of a cDNA clone specific for the oligodendrocyte-derived repulsive extracellular matrix molecules J1-160/180. J Neurosci Res. 1991 July; 29(3): 299-307

Fuss B, Bartsch U, Wintergerst E S, Pesheva P, Schachner M. Characterization of the neural recognition molecule janusin J1-160/180). Schweiz Arch Neurol Psychiatr. 1993; 144(3): 197-8

GrandPre T, Nakamura F, Vartanian T, Strittmatter S M. Identification of the Nogo inhibitor of axon regeneration as a reticulon protein. Nature. 2000 Jan. 27; 403: 439-44

Heape A M, Lehto V P, Kursula P. The expression of recombinant large myelin-associated glycoprotein cytoplasmic domain and the purification of native myelin-associated glycoprotein from rat brain and peripheral nerve. Protein Expr Purif 1999 April;15(3):349-61.

Hong S S, Boulanger P. Protein ligands of the human adenovirus type 2 outer capsid identified by biopanning of a phage-displayed peptide library on separate domains of wild-type and mutant penton capsomers. EMBO J 1995 Oct. 2;14(19):4714-27.

Huang D W, Mckerracher L, Braun P E, David S. A therapeutic vaccine approach to stimulate axon regeneration in the adult mammalian spinal cord. Neuron. 1999 November; 24(3): 639-47

Hyde-DeRuyscher R, Paige L A, Christensen D J, Hyde-DeRuyscher N, Lim A, Fredericks Z L, Kranz J, Gallant P, Zhang J, Rocklage S M, Fowlkes D M, Wendler P A, Hamilton P T. Detection of small-molecule enzyme inhibitors with peptides isolated from phage-displayed combinatorial peptide libraries. Chem Biol 2000 January;7(1): 17-25.

Kukel-Bagden E, Dai H N, Bregman B S. Methods to assess the development and recovery of locomotor function after spinal cord injury in rat. Exp Neurol. 1993; 119: 153-64

Lagenaur C, Lemmon V. An Li-like molecule, the 8D9 antigen, is a potent substrate for neurite extension. Proc Natl Acad Sci USA. 1987 November;84(21):7753-7

Li M, Shibata A, Li C, Braun P E, Mckerracher L, Roder J, Kater S B, David S. Myelin-associated glycoprotein inhibits neurite/axon growth and causes growth cone collapse. J Neurosci Res. 1996 Nov. 15: 46(4): 404-14

Li G L, Farooque M. Expression of ubiquitin-like immunoreactivity in axons after compression trauma to rat spinal cord. Acta Neuropathol (Berl) 1996;91(2):155-60.

Lochter A, Schachner M. Tenascin and extracellular matrix glycoproteins: from promotion to polarization of neurite growth in vitro. J Neurosci. 1993 September; 13(9): 3986-4000

Mckerracher L, David S, Jackson D L, Kottis V, Dunn R J, Braun P E. Identification of myelin-associated glycoprotein as a major myelin-derived inhibitor of neurite growth. Neuron. 1994 October; 13(4):805-11

Merkler D, Metz G A, Raineteau O, Dietz V, Schwab M E, Fouad K. Locomotor recovery in spinal cord-injured rats treated with an antibody neutralizing the myelin-associated neurite growth inhibitor Nogo-A. J Neurosci 2001 May 15;21(10):3665-73.

Motti C, Nuzzo M, Meola A, Galfre G, Felici F, Cortese R, Nicosia A, Monaci P. Recognition by human sera and immunogenicity of HBsAg mimotopes selected from an M13 phage display library. Gene 1994 Sep. 2;146(2):191-8.

Mukhopadhyay G, Doherty P, Walsh F S, Crocker P R, Filbin M T. A novel role for myelin-associated glycoprotein as an inhibitor of axonal regeneration. Neuron. 1994 September; 13(3): 757-67

Nilsson M T, Mossing M C, Widersten M. Functional expression and affinity selection of single-chain cro by phage display: isolation of novel DNA-binding proteins. Protein Eng 2000 July;13(7) :519-26.

Pesheva P, Spiess E, Schachner M. J1-160 and J1-180 are oligodendrocyto-secreted nonpermissive substrates for cell adhesion. J Cell biol. 1989 October; 109(4 Pt 1): 1765-78

Pesheva P, Gennarini G, Goridis C, Schachner M. The F3/11 cell adhesion molecule mediates the repulsion of neurons by the extracellular matrix glycoprotein J1-160/180. Neuron. 1993 January; 10(1): 69-82

Pesheva P, Probstmeier R. The yin and yang of tenascin-R in CNS development and pathology. : Prog Neurobiol 2000 August;61(5):465-93.

Pesheva P, Gloor S, Probstmeier R. Tenascin-R as a regulator of CNS glial cell function. Prog Brain Res 2001;132:103-14.

Rodriguez M, Lennon V A, Benveniste E N, Merrill J E. Remyelination by oligodendrocytes stimulated by antiserum to spinal cord. J Neuropathol Exp Neurol 1987 January;46(1):84-95.

Schwab M E. Experimental aspects of spinal cord regeneration. Curr Opin Neurol Neurosurg. 1993 August; 6(4): 549-53

Scott J K, Smith G P. Searching for peptide ligands with an epitope library. Science 1990 Jul. 27;249(4967):386-90.

Shen Y J, DeBellard M E, Salzer J L, Roder J, Filbin M T. Myelin-associated glycoprotein in myelin and expressed by Schwann cells inhibits axonal regeneration and branching. Mol Cell Neurosci 1998 September;12(1-2):79-91.

Smith G P. Filamentous fusion phage: novel expression vectors that display cloned antigens on the virion surface. Science 1985 Jun. 14;228(4705):1315-7.

Tang S, Woodhall R W, Shen Y J, deBellard M E, Saffell J L, Doherty P, Walsh F S, Filbin M T. Soluble myelin-associated glycoprotein (MAG) found in vivo inhibits axonal regeneration. Mol Cell Neurosci 1997;9(5-6):333-46.

Tang S, Shen Y J, DeBellard M E, Mukhopadhyay G, Salzer J L, Crocker P R, Filbin M T. Myelin-associated glycoprotein interacts with neurons via a sialic acid binding site at ARG118 and a distinct neurite inhibition site. J Cell Biol 1997 Sep. 22;138(6):1355-66.

Tang S, Qiu J, Nikulina E, Filbin M T. Soluble myelin-associated glycoprotein released from damaged white matter inhibits axonal regeneration. Mol Cell Neurosci 2001 September;18(3) :259-69.

Taylor J, Pesheva P, Schachner M. Influence of janusin and tenascin on growth cone behavior in vitro. J Neurosci Res. 1993 Jul. 1; 35( 4 ): 347-62

Turnley A M, Bartlett P F. MAG and MOG enhance neurite outgrowth of embryonic mouse spinal cord neurons. : Neuroreport 1998 Jun. 22;9(9):1987-90.

Wintergerst E S, Fuss B, Bartsch U. Localization of janusin mRNA in the central nervous system of the developing and adult mouse. Eur J Neurosci. 1993 Apr. 1; 5(4): 299-310

Wintergerst E S, Bartsch U, Batini C, Schachner M. Changes in the expression of the extracellular matrix molecules tenascin-C and tenascin-R after 3-acetylpyridine-induced lesion of the olivocerebellar system of the adult rat. Eur J Neurosci 1997 March;9(3):424-34.

Xiao Z C, Taylor J, Montag D, Rougon G, Schachner M. Distinct effects of recombinant tenascin-R domains in neuronal cell functions and identification of the domain interacting with the neuronal recognition molecules F3/11. Eur J Neurosci. 1996; 8: 766-82

Xiao Z C, Hillenbrand R, Schachner M, Thermes S, Rougon G, Gomaz S. Signalling events involved following the interaction of the neuronal adhesion molecule F3 with the EGF-L domain of tenascin-R. J Neurosci Res. 1997; 39: 698-709

Xiao Z C, Revest J M, Laeng P, Rougon G, Schachner M, Montag D. Defasciculation of cerebellar neurons is mediated by tenascin-R and its neuronal receptor, the immunoglobulin superfamily molecule F3/F11. J Neurosci Res. 1998; 52: 390-404.

Yang H, Xiao Z C, Becker B, Hillenbrand R, Rougon G, Schachner M. Role for myelin-associated glycoprotein as a functional tenascin-R receptor. J Neurosci Res 1999 Mar. 15;55(6):687-701.

The invention claimed is:

1. An isolated peptide of up to 8 amino acids in length comprising the amino acid sequence of YLTQPQS (SEQ ID NO: 1), wherein the peptide has binding affinity for one or more neuronal growth inhibitor molecules selected from the group consisting of Nogo, Nogo-66 and myelin-associated glycoprotein (MAG).

2. An isolated peptide consisting of the amino acid sequence of YLTQPQS (SEQ ID NO: 1).

3. A composition for the treatment of spinal cord injury comprising one or more peptides selected from the group consisting of
   (a) a peptide consisting of the amino acid sequence of YLTQPQS (SEQ ID NO: 1); and
   (b) a peptide of up to 8 amino acids in length comprising the amino acid sequence of YLTQPQS (SEQ ID NO: 1),
   wherein the peptide of (b) has binding affinity for one or more neuronal growth inhibitor molecules selected from the group consisting of Nogo, Nogo-66 and myelin-associated glycoprotein (MAG);
   together with one or more pharmaceutically acceptable ingredients, said composition optionally being formulated for injection.

4. A method for treating spinal cord injury in a patient in need thereof comprising administering an effective amount of the composition of claim 3 intrathecally in the patient.

5. A method as claimed in claim 4, wherein said damage is caused by a neuronal growth inhibitory molecule selected from the group consisting of Nogo, Nogo-66 and myelin-associated glycoprotein (MAG).

* * * * *